(12) United States Patent
Lifshitz-Liron et al.

(10) Patent No.: US 7,074,928 B2
(45) Date of Patent: Jul. 11, 2006

(54) POLYMORPHS OF CLOPIDOGREL HYDROGENSULFATE

(75) Inventors: Revital Lifshitz-Liron, Herzlia (IL); Eti Kovalevski-Ishai, Netanya (IL); Shlomit Wizel, Petah Tiqva (IL); Sharon Avhar-Maydan, Givataym (IL); Rami Lidor-Hadas, Kfar Saba (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 370 days.

(21) Appl. No.: 10/339,008

(22) Filed: Jan. 8, 2003

(65) Prior Publication Data

US 2003/0225129 A1 Dec. 4, 2003

Related U.S. Application Data

(63) Continuation-in-part of application No. 10/074,409, filed on Feb. 12, 2002, now Pat. No. 6,767,913, and a continuation-in-part of application No. PCT/US02/40679, filed on Dec. 18, 2002.

(60) Provisional application No. 60/359,157, filed on Feb. 21, 2002, and provisional application No. 60/348,182, filed on Jan. 11, 2002.

(51) Int. Cl.
C07D 47/02 (2006.01)

(52) U.S. Cl. ........................ 546/119; 546/120
(58) Field of Classification Search .............. 514/301; 546/119, 120
See application file for complete search history.

(56) References Cited

U.S. PATENT DOCUMENTS

| | | | |
|---|---|---|---|
| 4,529,596 A | 7/1985 | Aubert et al. | |
| 4,847,265 A | 7/1989 | Badorc et al. | |
| 5,036,156 A | 7/1991 | Bouisset et al. | |
| 5,132,435 A | 7/1992 | Bousquet et al. | |
| 5,204,469 A | 4/1993 | Descamps et al. | |
| 5,576,328 A | 11/1996 | Herbert et al. | |
| 6,080,875 A | 6/2000 | Castro et al. | |
| 6,180,793 B1 | 1/2001 | Bakonyi et al. | |
| 6,215,005 B1 | 4/2001 | Heymes et al. | |
| 6,258,961 B1 | 7/2001 | Bakonyi et al. | |
| 6,429,210 B1 | 8/2002 | Bousquet et al. | |
| 6,504,030 B1 | 1/2003 | Bousquet et al. | |
| 2002/0177712 A1 | 11/2002 | Pandey et al. | |
| 2002/0198229 A1 | 12/2002 | Bousquet et al. | |

FOREIGN PATENT DOCUMENTS

| | | |
|---|---|---|
| EP | 0 281 459 | 9/1988 |
| FR | 2 769 313 | 4/1999 |
| WO | WO 98/04259 | 2/1998 |
| WO | WO 98/09286 | 9/1998 |
| WO | WO 98/39322 | 9/1998 |
| WO | WO 98/51681 | 11/1998 |
| WO | WO 98/51682 | 11/1998 |
| WO | WO 98/51689 | 11/1998 |
| WO | WO 99/18110 | 4/1999 |
| WO | WO 99/65915 | 12/1999 |
| WO | WO 00/27840 | 5/2000 |
| WO | WO 00/66130 | 11/2000 |
| WO | WO 02/059128 | 8/2002 |

OTHER PUBLICATIONS

Reist et al., "Very Slow Chiral Inversion of Clopidogrel in Rats: A Pharmacokinetic and Mechanistic Investigation," Drug Metabolism and Disposition, vol. 28, No. 12, Sep. 11, 2000, pp. 1405–1410.

Harry G. Brittain (Editor) "Polymorphism in Pharmaceutical Solids" Drugs and the Pharmaceutical Sciences, vol. 95, (1999) Marcel Dekker, Inc., New York, New York.

*Primary Examiner*—Cecila J. Tsang
*Assistant Examiner*—Raymond Covington
(74) *Attorney, Agent, or Firm*—Kenyon & Kenyon

(57) ABSTRACT

Provided are new crystalline Forms III, IV, V and VI of clopidogrel hydrogensulfate and the amorphous form of clopidogrel hydrogensulfate, as well as their pharmaceutical compositions, and method of treatments with such compositions. Also provided are novel processes for preparation of clopidogrel hydrogensulfate Form I, Form II, Form III, Form IV, Form V, Form VI and amorphous form.

35 Claims, 15 Drawing Sheets

DSC THERMOGRAM OF CLOPIDOGREL HYDROGENSULFATE FORM III

FIG. 3 FTIR SPECTRUM OF CLOPIDOGREL HYDROGENSULFATE FORM III

FIG. 5 FTIR SPECTRUM OF CLOPIDOGREL HYDROGENSULFATE AMORPHOUS FORM

| RRT | 0.11 | 0.12 | 0.14 | 0.15 | 0.16 | 0.55 | 0.77-0.79 AMINO-PREC. | 1.00 CLD | 1.15 | 1.24 | 2.25 |
|---|---|---|---|---|---|---|---|---|---|---|---|
| FORM IV* |  | 0.08 | 0.12 |  |  |  | 0.09 | 100.0 |  |  |  |
| FORM VI |  | 0.23 | 0.06 | 0.08 |  |  | 0.10 | 98.6 | 0.14 | 0.28 | 0.33 |
| FORM III* |  |  |  |  | 0.61 |  |  | 98.5 | 0.15 |  |  |
| FORM V* |  |  |  | 0.22 | 0.72 |  |  | 99.4 | 0.15 | 0.21** |  |

NOTE: ONLY PEAKS WITH AREA>0.044% ARE INCLUDED IN THIS TABLE
*SAMPLES AFTER ADDITIONAL DRYING, 24 H AT 60 CELSIUS & 24 H AT 70 CELSIUS.
**PEAK FROM PREVIOUS INJECTION
ALL THE SAMPLES WILL BE INJECTED AGAIN, FOR 120 MINUTES
THE SAMPLE FOR FORM III CORRESPONDS TO EXAMPLE 26, FORM IV TO EXAMPLE 31, FORM V TO EXAMPLE 39 AND FORM VI TO EXAMPLE 44.

IMPURITY PROFILE FOR CLOPIDOGREL HYDROGENSULFATE

FIG. 15

POLYMORPHS OF CLOPIDOGREL HYDROGENSULFATE

CROSS-REFERENCE TO RELATED APPLICATIONS

This application is a continuation-in-part of application Ser. No. 10/074,409, filed on Feb. 12, 2002 now U.S. Pat. No. 6,767,915, and is a continuation of PCT/US02/40679, filed on Dec. 18, 2002, and claims benefit of 60/348,182 filed on Jan. 11, 2002 and 60/359,157, filed on Feb. 21, 2002. All of which are incorporated herein by reference.

FIELD OF THE INVENTION

The present invention relates to the solid state chemistry of clopidogrel hydrogensulfate.

BACKGROUND OF THE INVENTION

Atherosclerosis is the buildup of plaque in the wall of the arteries leading to a thickening and a reduction in elasticity of the arteries. Atherosclerosis results from injury to the inside layer of the artery. The injury is caused by common activities and diseases such as high cholesterol, high blood pressure, smoking and infection.

Plaques form on the inner walls of the artery at these sites of injury. The plaques are mainly composed of fatty tissue and smooth muscle cells. The formation of plaque often leads to blood clotting due to platelet aggregation at the site of the injury. This clotting may result in a reduction or elimination of blood flow to vital organs, causing heart attacks or other serious conditions. The plaque may also rupture and send a blood clot through the artery, referred to as an embolus, which if deposited in a smaller blood vessel may completely block blood flow.

Antiplatelet activity is desirable in fighting the often fatal results of atherosclerosis. Clopidogrel is an inhibitor of induced platelet aggregation which act by inhibiting the binding of adenosine diphosphate to its receptor. Clopidogrel is metabolized by the liver into active form. Its antiplatelet activity is extended in that it stops any platelet activity even up to ten days after administration.

The chemical name of clopidogrel is methyl (+)-(S)-α-(o-chlorophenyl)-6,7-dihydrothieno[3,2-c]pyridine-5(4H)-acetate. It has the following structure:

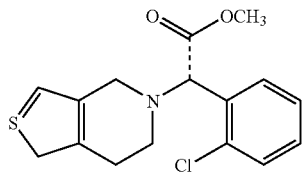

Clopidogrel's platelet inhibiting activity makes it an effective drug for reducing the incidence of ischemic strokes, heart attacks or claudication due to vascular diseases such as atherosclerosis. By inhibiting platelet aggregation, clopidogrel reduces the chance of arterial blockage, thus preventing strokes and heart attacks. U.S. Pat. No. 5,576,328 describes a method of preventing the occurrence of a secondary ischemic event by administration of clopidogrel, and is incorporated herein as a reference.

Recent studies have shown that clopidogrel is more effective in blocking platelet aggregation than aspirin and is much gentler on the gastrointestinal tract. Clopidogrel is more effective than aspirin even at much lower dosage. A dosage of 75 mg of base equivalent has been shown to be more effective than a dosage of 325 mg of aspirin. In addition to being more effective, clopidogrel produces much less gastrointestinal bleeding than aspirin.

Clopidogrel is administered as its hydrogensulfate (syn. bisulfate) salt. Clopidogrel hydrogensulfate has an empirical formula of $C_{16}H_{16}Cl\ NO_2S.H_2SO_4$. It is currently being marketed as PLAVIX® tablets, which contain about 98 mg clopidogrel hydrogensulfate, which is the equivalent of 75 mg clopidogrel base. PLAVIX® is a white to off-white powder that is practically insoluble in water at neutral pH but highly soluble at acidic pH. It dissolves freely in methanol, somewhat in methylene chloride, and poorly in ethyl ether. U.S. Pat. Nos. 4,847,265; 5,132,435; 6,258,961; 6,215,005 and 6,180,793, which are hereby incorporated by reference in their entirety, disclose methods that can be used to prepare clopidogrel hydrogensulfate.

The present invention relates to the solid state physical properties of clopidogrel hydrogensulfate prepared by any of these or other methods. These properties can be influenced by controlling the conditions under which clopidogrel is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account when developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences because it imposes an upper limit on the rate at which an orally-administered active ingredient can reach the bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC), and can be used to distinguish some polymorphic forms from others. A particular polymorphic form may also give rise to distinct properties that may be detectable by powder X-ray diffraction, solid state $^{13}C$ NMR spectrometry and infrared spectrometry.

The discovery of new crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

U.S. Pat. No. 4,529,596 is directed to the composition of clopidogrel and methods of its use. The 596 patent teaches synthesis of clopidogrel, but fails to suggest or disclose the existence of polymorphs or the amorphous form of clopidogrel. U.S. Pat. No. 4,847,265 is directed to the enantiomer of clopidogrel, and also does not suggest or teach any polymorphs or the amorphous form of clopidogrel. These U.S. patents are incorporated herein by reference.

International Publication No. WO 99/65915 discloses two polymorphs of clopidogrel hydrogensulfate, referred to as Forms I and II, though Form I is originally disclosed in EP 281459.

According to the International Publication No. WO 99/65915, Form I has a PXRD pattern with peaks at 9.2, 10.9, 15.2, 17.9, 18.5, 20.6, 23.0, 23.2, 23.4 and 25.5±0.2 degrees two theta. Form I also has an infrared spectrum with absorption bands at 2987, 1753, 1222, 1175 and 841 cm$^{-1}$.

WO 99/65915 also discloses clopidogrel hydrogensulfate Form II, according to which has a PXRD pattern with peaks at 12.9, 13.6, 15.6, 17.7, 19.5, 21.6, 23.0, 23.3 and 24.7±0.2 degrees two theta. It has an infrared spectrum with absorption bands at 2551, 1753, 1497, 1189 and 1029 cm$^{-1}$.

According to Applicants' English translation, in Example 1B, Form I is prepared by dissolving clopidogrel camphorsulfonate in dichloromethane under a nitrogen atmosphere. A solution of potassium carbonate in water is then introduced. The organic phase is then removed, concentrated and added to acetone. The acetone solution is placed in a reactor under nitrogen and a 94% solution of concentrated sulfuric acid is added. The mixture is then distilled and cooled, followed by subsequent crystallization. The crystals are washed and dried to obtain Form I.

According to Chemical Abstract Accession No. 1999:811251, Form II is prepared by addition of a solution of 50 g of clopidogrel camphorsulfonate in 100 mL of dichloromethane to a solution of 9.1 g of potassium carbonate in 70 mL of water. The organic phase was separated, concentrated and dissolved in 229 mL of acetone. The acetone solution was refluxed with 7.4 g of 80% sulfuric acid under nitrogen for 2 h. The solvent was then removed to yield Form II.

Form II may also be prepared from Form I by storing aqueous mother liquor from the crystallization of Form I for 3–6 months.

Four new crystal forms of clopidogrel hydrogensulfate, designated Forms III, IV, V and VI plus the amorphous form of clopidogrel hydrogensulfate, and a novel process for their preparation, and preparation of Form I and II of clopidogrel have now been discovered.

SUMMARY OF THE INVENTION

In one aspect, the present invention provides for clopidogrel hydrogensulfate characterized by data selected from the group consisting of a powder X-ray diffraction pattern with peaks at about 8.3, 9.1, 23.2, 23.6±0.2 degrees two-theta, a differential scanning calorimetric thermogram having an endothermic peak at about 136° C. and a FTIR spectrum with peaks at about 959, 1061, 1430, 1751, 1757 and 3119 cm$^{-1}$. Said crystalline form denotes Form VI.

In another aspect, the present invention provides a process for preparing clopidogrel hydrogensulfate comprising the steps of preparing a solution of clopidogrel hydrogensulfate in 1-propanol, removing the 1-propanol from the solution to obtain a residue, admixing an antisolvent with the residue to precipitate clopidogrel hydrogensulfate and separating the clopidogrel hydrogensulfate.

Preferably, removing is carried out in the processes of the present invention by evaporation.

In another aspect, the present invention provides a process for preparing clopidogrel hydrogensulfate Form II comprising the steps of preparing a solution of clopidogrel hydrogensulfate in a solvent selected from the group consisting of dichloromethane, 1,4-dioxane, toluene, chloroform, ethyl acetate, methylethyl ketone and t-butylmethyl ether, precipitating clopidogrel hydrogensulfate from the solution and separating the clopidogrel hydrogensulfate.

In another aspect, the present invention provides a process for preparing clopidogrel hydrogensulfate Form II comprising the steps of preparing a solution of clopidogrel hydrogensulfate in acetonitrile, admixing the solution with an antisolvent to precipitate clopidogrel hydrogensulfate and separating the precipitate.

Preferred anti-solvents are $C_2$ to $C_8$ ethers.

The present invention also provides for clopidogrel hydrogensulfate 1-propanolate.

The present invention also provides for pharmaceutical compositions and their method of administration to inhibit platelet aggregation.

BRIEF DESCRIPTION OF THE FIGURES

FIG. 15 is an area analysis of impurities using HPLC.

DETAILED DESCRIPTION OF THE INVENTION

As used herein, the terms "IPA", "isopropanol", "isopropyl alcohol" and "2-propanol" refer to the same alcohol.

As used herein, the terms "crystallization" and "precipitation" are synonymous.

The present invention provides new polymorphs of clopidogrel hydrogensulfate and novel amorphous form. The various forms are obtained inter alia by using different alcohols.

Figure 1:
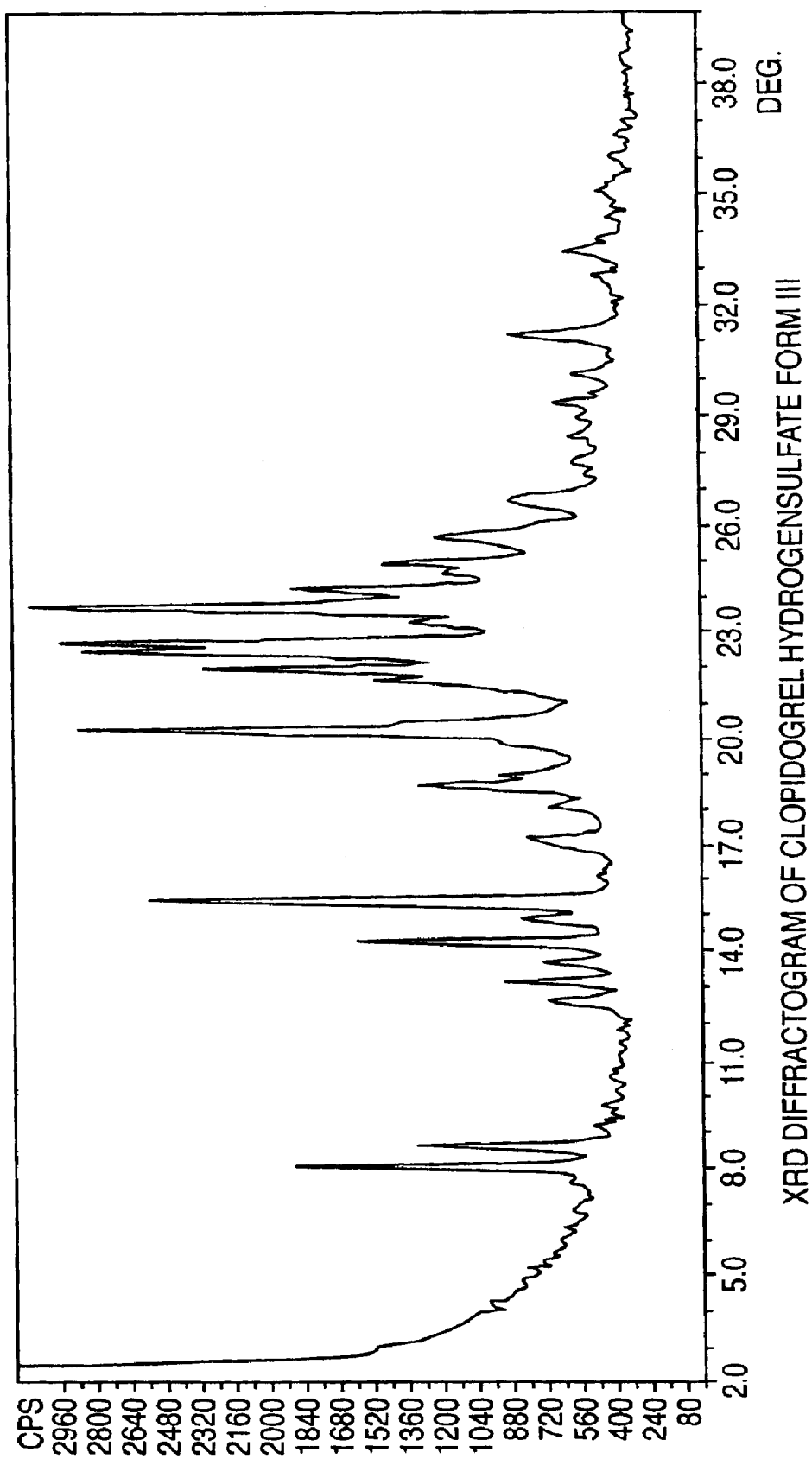
FIG. 1 is a powder X-ray diffraction pattern of clopidogrel hydrogensulfate Form III.

In a first aspect, the present invention provides a new crystalline form of clopidogrel hydrogensulfate, designated Form III. Clopidogrel hydrogensulfate Form III is characterized by a powder X-ray diffraction pattern (FIG. 1) with peaks at about 8.1, 8.7, 14.3, 15.4, 20.1, 22.3, 22.5, 23.5, and 24.1±0.2 degrees two-theta.

Figure 2:
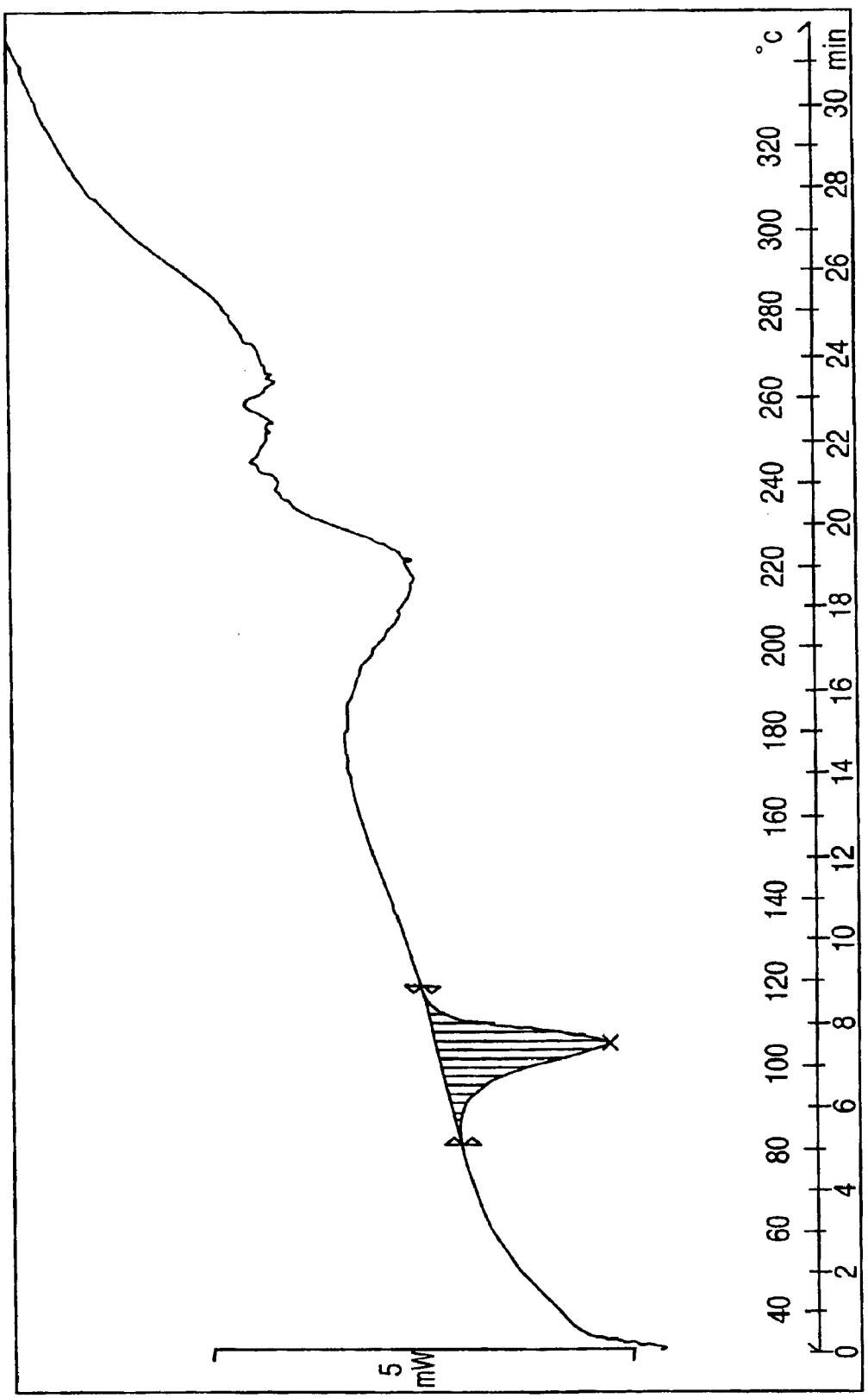
FIG. 2 is a differential scanning calorimetric (DSC) thermogram of clopidogrel hydrogensulfate Form III.

Clopidogrel hydrogensulfate Form III produces a differential scanning calorimetric (DSC) thermogram (FIG. 2) having a maximum endotherm of about 105° C.

Figure 3:
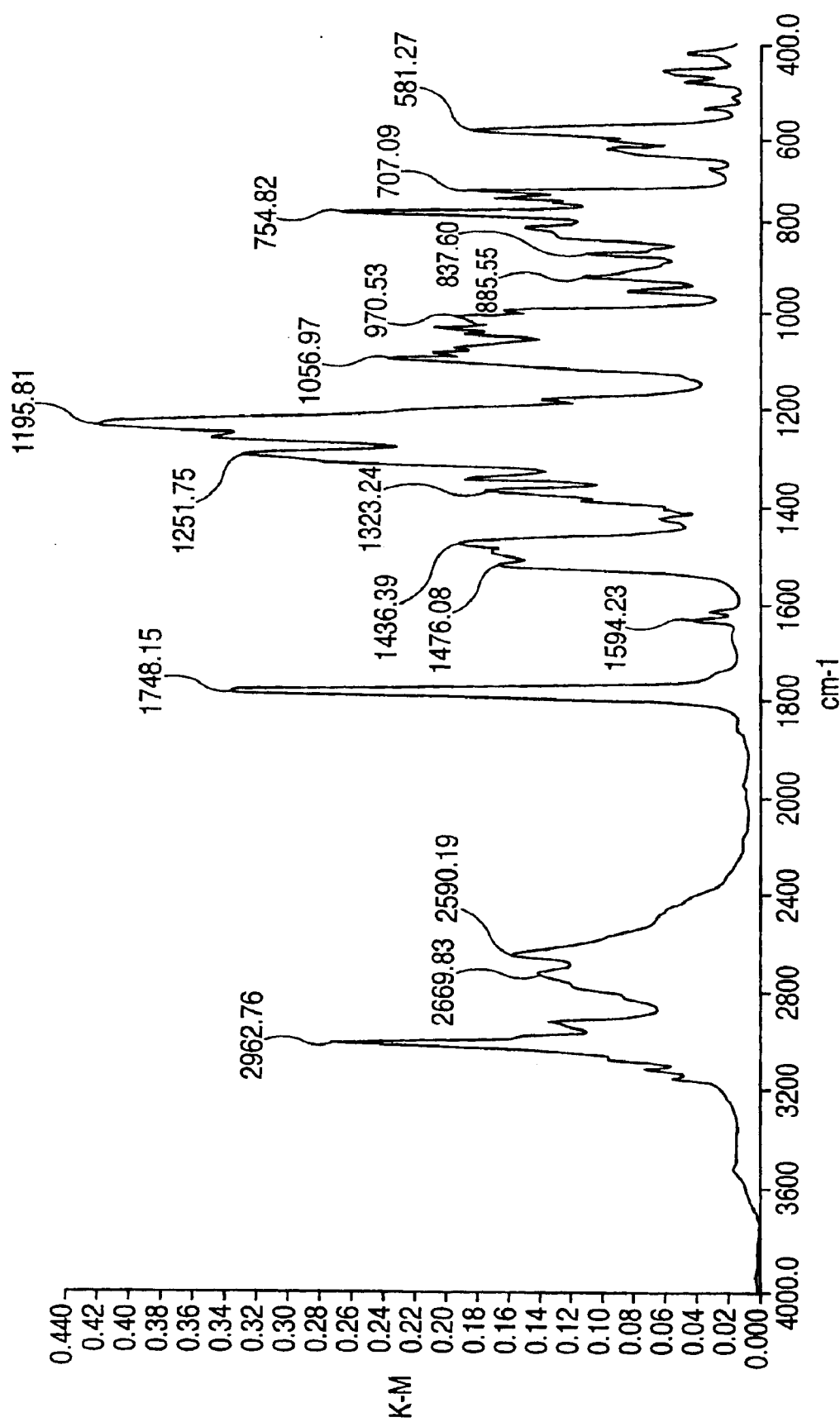
FIG. 3 is a FTIR spectrum of clopidogrel hydrogensulfate Form III.

Clopidogrel hydrogensulfate Form III produces a FTIR spectrum (FIG. 3) with characteristic absorption bands at about 581, 707, 755, 971, 1057, 1196, 1252, 1436, 1476, 1748, 2590, 2670 and 2963 $cm^{-1}$. The FTIR spectrum of clopidogrel hydrogensulfate Form III has additional absorption bands at about 838, 886 and 1594 $cm^{-1}$.

The present invention further provides a process for preparing clopidogrel hydrogensulfate Form III comprising the steps of preparing a solution of clopidogrel hydrogensulfate and 1-butanol, removing the 1-butanol to obtain a residue, admixing an antisolvent with the residue to precipitate clopidogrel hydrogensulfate and separating the clopidogrel hydrogensulfate.

In the process, clopidogrel hydrogensulfate is mixed with a sufficient amount of alcohol to dissolve the clopidogrel hydrogensulfate at or below the reflux temperature of the alcohol. To fully dissolve the clopidogrel hydrogensulfate, the mixture may be heated to a temperature up to reflux of the alcohol. Preferably, the mixture is refluxed for about 30 minutes. When preparing the solution with clopidogrel base and sulfuric acid, the solution is preferably refluxed for longer periods of time, such as about 2 hours. One skilled in the art may appreciate that minor differences in the temperature and times may produce the same result, and other temperatures and times may produce the same result under other conditions.

In the most preferred embodiment, the alcohol is evaporated under ambient or reduced pressure after cooling, with intermediate cooling optional. Preferably, the solution is cooled to room temperature and the alcohol is evaporated under reduced pressure. A residue remains after evaporation.

An antisolvent is then added to the residue. Preferably, the antisolvent is ether. More preferably, each one of the ether's alkyl radical groups connected to the oxygen atom is independently selected from the group consisting of methyl, ethyl, propyl, isopropyl, butyl, 1-butyl, 2-butyl and t-butyl. Most preferably, the ether is diethyl ether or methyl t-butyl ether.

The mixture of residue and antisolvent may then be stirred for one or two days, preferably for longer times when starting with clopidogrel base. A precipitate begins to form. The precipitate is then separated from the mixture. One skilled in the art may appreciate that there are many ways to separate the precipitate from the mixture. Preferably, the precipitate is separated by filtration. After separation, the precipitate may optionally be washed with an organic solvent such as diethyl ether to remove impurities.

The separated precipitate in then preferably dried, under either ambient or reduced pressure. In a preferred embodiment, the precipitate is dried under a vacuum. Preferably, the precipitate is heated to accelerate the drying process. More preferably, it is heated from about 40° C. to about 80° C. Most preferably, it is heated to about 50° C.–65° C. for about 24 hours in a vacuum oven. One skilled in the art may appreciate that many ways exist for drying a compound, and that by manipulating the conditions, other temperatures, pressures and time periods would suffice.

Clopidogrel Form III may be obtained in yields of about 97%, which shows the high efficiency and effectiveness of this novel process.

In another aspect, the present invention provides novel amorphous clopidogrel hydrogensulfate. In accordance with the invention, amorphous clopidogrel hydrogensulfate is highly pure. More preferably, it is essentially free of crystalline clopidogrel hydrogensulfate. Most preferably, the amorphous clopidogrel hydrogensulfate is free of crystalline clopidogrel hydrogensulfate within the detection limits of a powder X-ray diffractometer comparable to the instrumentation described. The purity of clopidogrel hydrogensulfate can be assessed by a comparison of the PXRD pattern of an unknown sample with those of mixtures of authentic pure amorphous and authentic pure crystalline clopidogrel hydrogensulfate.

Figure 4:
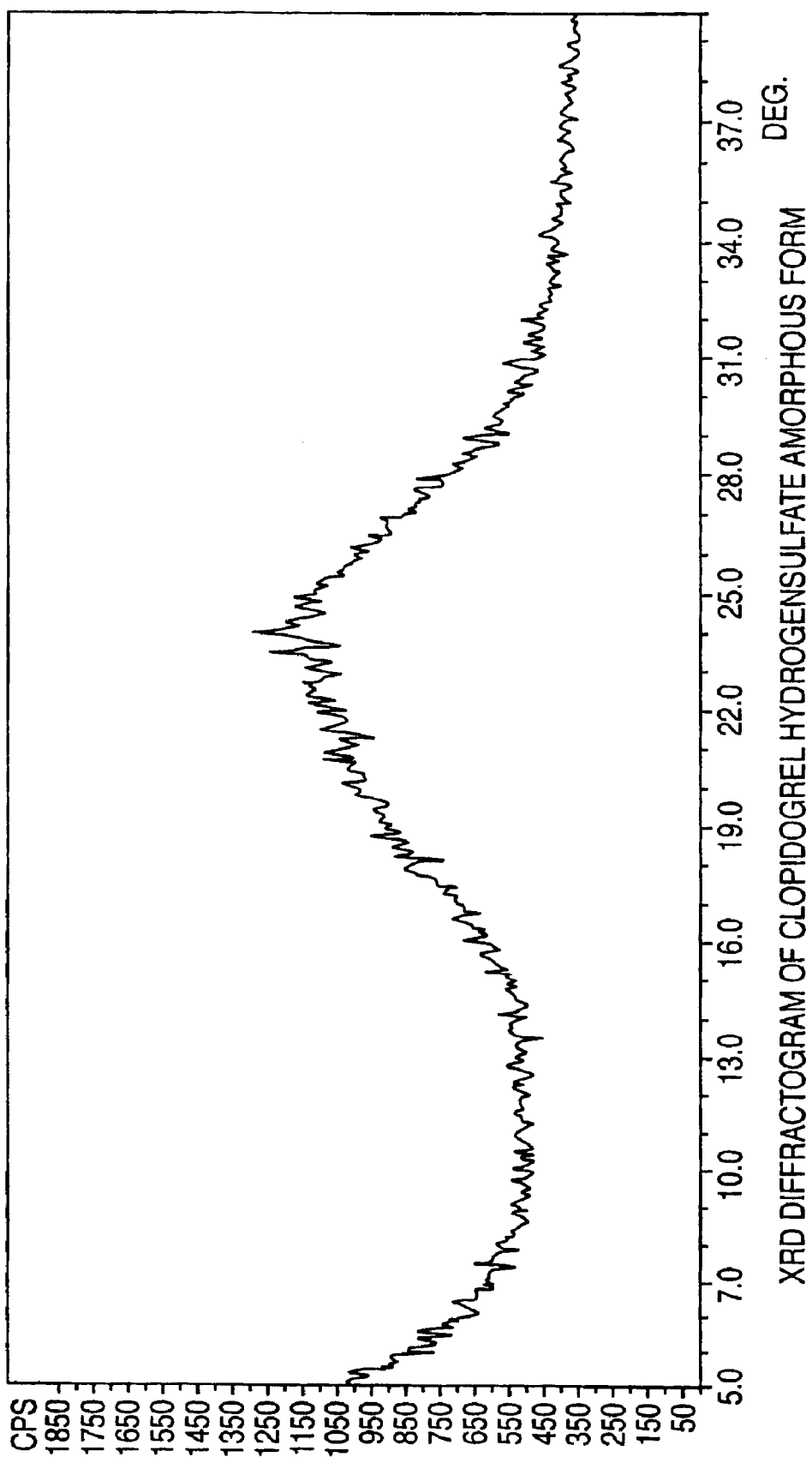
FIG. 4 is a powder X-ray diffraction (PXRD) pattern of clopidogrel hydrogensulfate amorphous form.

The amorphous character and purity of the material we have produced is confirmed by a powder X-ray diffraction pattern obtained from a sample thereof, which is provided as FIG. 4. The pattern is without intense focused reflections and is featureless except for a halo with a maximum centered at about 24 degrees two-theta.

Figure 5:
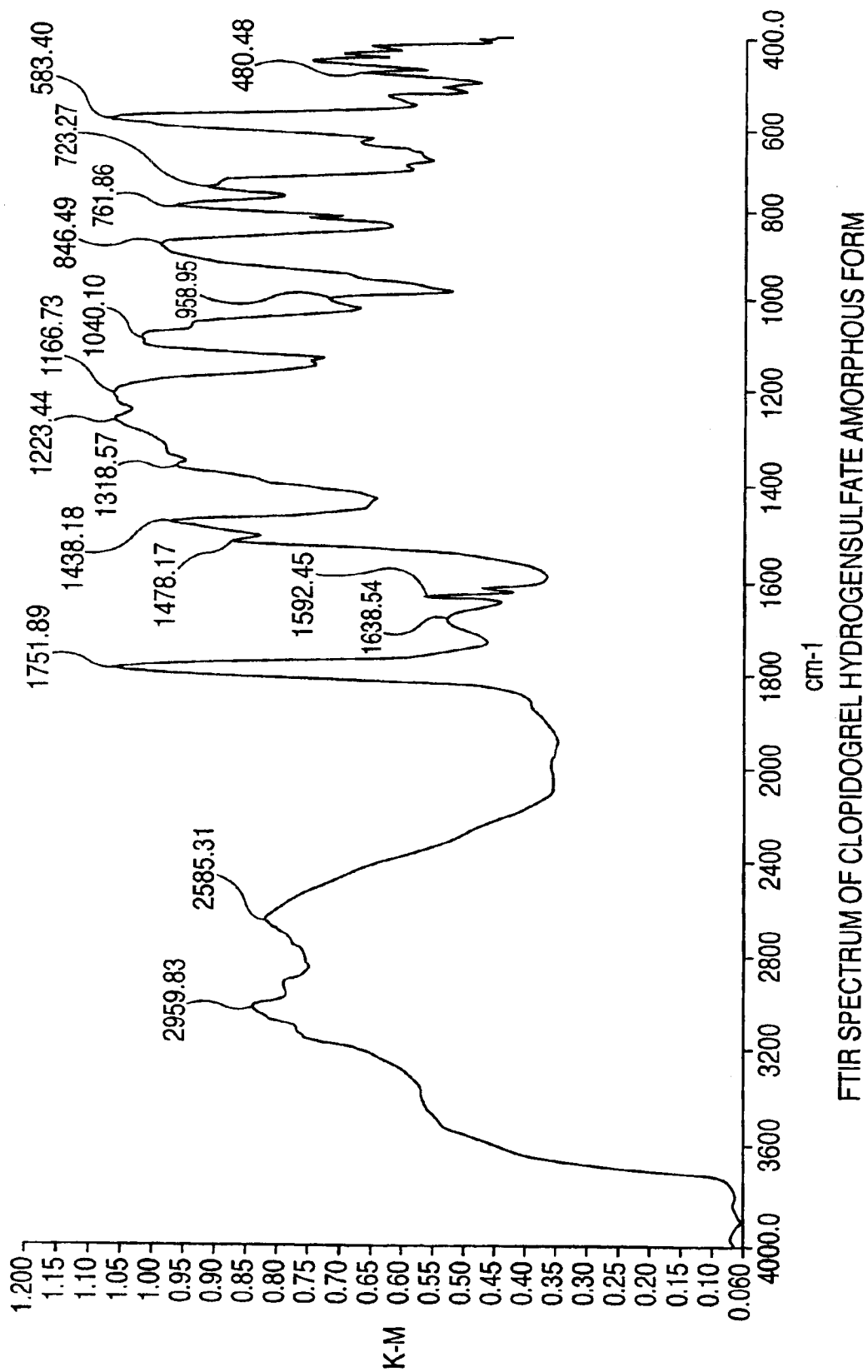
FIG. 5 is a FTIR spectrum of clopidogrel hydrogensulfate amorphous form.

The amorphous form has a FTIR spectrum (FIG. 5) with peaks at about 583, 723, 762, 846, 1040, 1167, 1223, 1438, 1478, 1638, 1752, 2585 and 2960 $cm^{-1}$.

The invention further provides a process for preparing amorphous form of clopidogrel hydrogensulfate comprising the steps of preparing a solution of clopidogrel hydrogensulfate in methanol or ethanol, and admixing the solution with an antisolvent to precipitate clopidogrel hydrogensulfate and separating the clopidogrel hydrogensulfate.

The alcoholic solution of clopidogrel hydrogensulfate may be heated to increase the solubility of clopidogrel hydrogensulfate in the alcohol. Preferably, the solution is heated from about room temperature to about reflux, with temperatures at or near reflux being most preferred. After dissolution, the solution may be cooled, preferably to room temperature.

The alcohol may optionally be removed from the solution to obtain a foam or an oily residue. Preferably, the alcohol is removed by evaporation. The alcohol may be evaporated under ambient or reduced pressure and optionally heated to accelerate the evaporation. The antisolvent in such a case is then added to the foam or the oily residue.

Alternatively, the solution of clopidogrel hydrogensulfate and alcohol may be added to the antisolvent to precipitate clopidogrel hydrogensulfate. Preferably, the solution is added slowly to the antisolvent. Preferably, the antisolvent is an ether. Each alkyl radical of the ether may be independently selected from the group consisting of methyl, ethyl, propyl, isopropyl, butyl, 1-butyl, 2-butyl and tert-butyl. In one preferred embodiment, the ether is methyl t-butyl ether. In another preferred embodiment, the ether is diethyl ether.

A precipitate forms in the ether. The precipitate should be separated from the ether at an early stage, preferably within a few hours. Otherwise, the amorphous form will change to Form 1, resulting in a lower yield.

The precipitate may be separated by techniques well-known in the art. Preferably, the precipitate is separated by filtration. Optionally, vacuum filtration may be utilized.

The precipitate may be dried under ambient or reduced pressure. Preferably, the precipitate is heated in a vacuum oven for about 24 hours. More preferably, the precipitate is heated to a temperature of about 40° C. to about 70° C. Most preferably, it is heated to about 50° C. for about 24 hours.

The present invention also provides a process for preparing amorphous clopidogrel hydrogensulfate comprising the steps of preparing a solution of clopidogrel hydrogensulfate in methanol or ethanol, admixing the solution with an antisolvent; and removing the alcohol and the antisolvent. Preferably, the solution is added to the anti solvent.

In one preferred embodiment, the antisolvent is a one ring aromatic hydrocarbon, such as toluene, benzene or xylene. Most preferably, the one ring aromatic hydrocarbon is toluene.

Clopidogrel hydrogensulfate is first dissolved in the alcohol to form a solution. After dissolving the clopidogrel hydrogensulfate in the alcohol, the solution is added to the antisolvent. In a less preferred embodiment, the solution is concentrated before addition to the antisolvent. Preferably, the antisolvent is heated to a temperature of about room temperature to reflux so that the clopidogrel hydrogensulfate becomes more soluble in the antisolvent, with temperatures at or near reflux being preferred. Most preferably, the antisolvent is heated to reflux temperature. Besides heating the antisolvent, the mixture may be added to the antisolvent at a substantially slow rate to increase the total amount of clopidogrel taken up by the antisolvent.

After addition of the mixture to the antisolvent, the resulting mixture is preferably cooled to about room temperature, though one skilled in the art may appreciate that other temperatures may achieve the same result. To obtain the amorphous form, the antisolvent and the alcohol are removed, preferably by evaporation, to leave the amorphous form. Evaporation may occur under ambient or reduced pressure, and the solution may be heated to accelerate the evaporation process.

The present invention provides a process for preparing the amorphous form of clopidogrel hydrogensulfate comprising the steps of preparing a solution of clopidogrel hydrogensulfate in acetone and removing acetone to obtain the amorphous form. The mixture of clopidogrel hydrogensulfate and acetone is heated to form a solution. Preferably, the mixture is heated to a temperature where a homogeneous solution forms. Most preferably, the mixture is heated to about reflux for a few hours.

After heating, the solution is preferably cooled to about room temperature. The solution may be stirred. Preferably, the solution is stirred for a few hours. After stirring, the acetone is removed to obtain a powder, which is the amorphous form of clopidogrel hydrogensulfate. Preferably, the acetone is removed by evaporation. To accelerate the drying process, the pressure may be reduced and the temperature may be raised. One skilled in the art would appreciate that preparation of the amorphous form may be possible under other conditions.

The present invention also provides a process for preparing clopidogrel hydrogensulfate Form I and mixtures of clopidogrel Form I and amorphous clopidogrel hydrogensulfate.

The amorphous form converts into Form I over time when contacted, preferably suspended, in an ether. Preferably, the ether is a $C_2$ to $C_8$ ether as described above, more preferably methyl t-butyl ether or diethyl ether. One skilled in the art may appreciate that the ratio of Form I to the amorphous form increases with time, and that, through routine experimentation, the ratio of the forms to each other may be determined for any specific time.

The examples illustrate that the amorphous form of clopidogrel hydrogensulfate undergoes a transformation to Form I in an ether, particularly in the time period from about 45 minutes to one hour. To obtain substantially Form I, clopidogrel hydrogensulfate is suspended in the ether for preferably one hour, with longer periods of time, such as four and eight hours, being most preferred. The transformation time may be longer if the starting material is clopidogrel free base rather than clopidogrel hydrogensulfate.

As the examples illustrate and one skilled in the art may appreciate, it is possible to obtain clopidogrel hydrogensulfate Form I from clopidogrel hydrogensulfate through the use of the amorphous form as an intermediate. First the amorphous form is obtained as illustrated, and then suspended in an ether to obtain Form I. The examples of the present invention obtain Form I through this mechanism.

Figure 6:
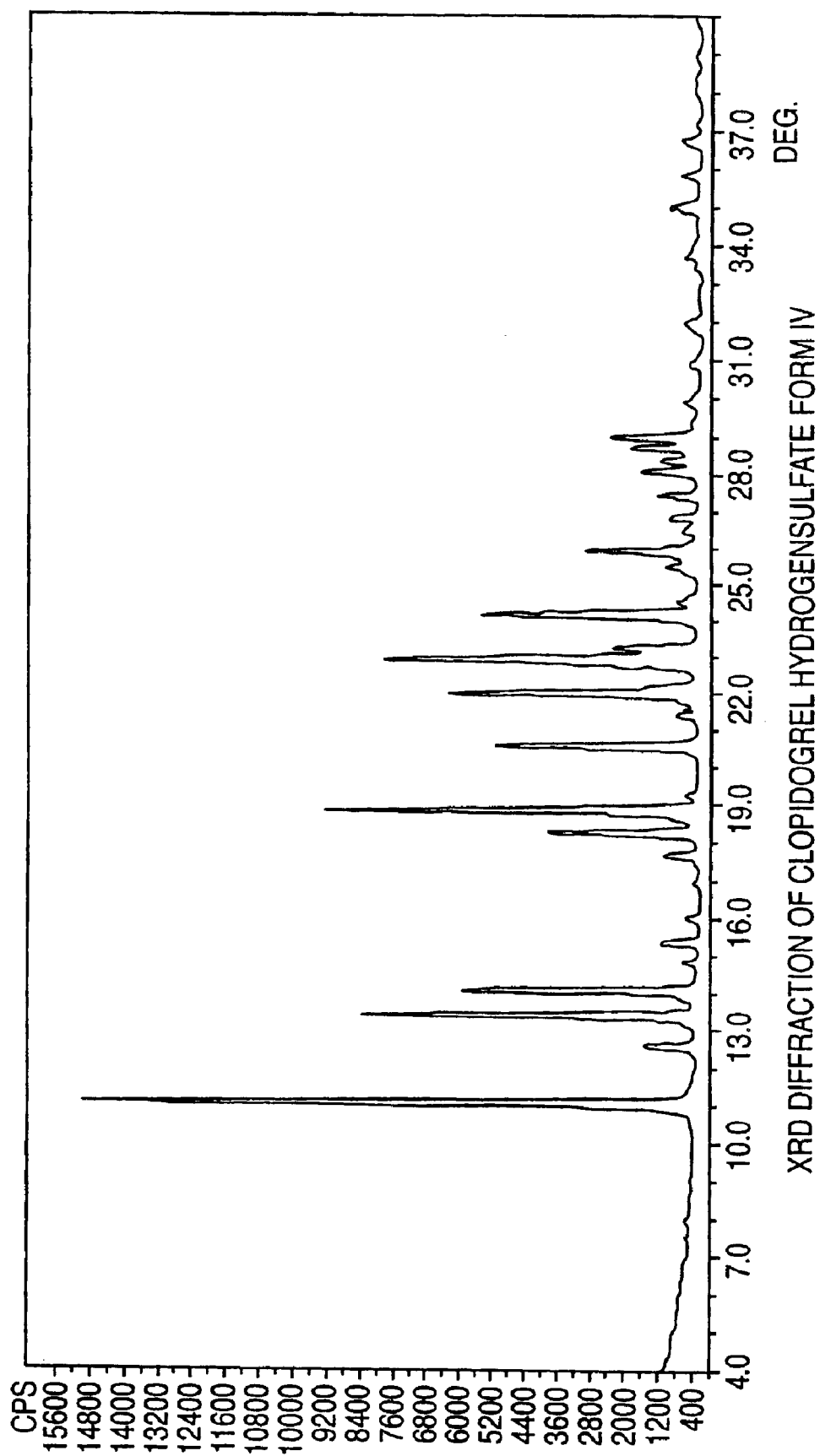
FIG. 6 is a PXRD pattern of clopidogrel hydrogensulfate Form IV.

The present invention also provides clopidogrel hydrogensulfate Form IV. Clopidogrel hydrogensulfate Form IV is characterized by powder X-Ray diffraction (PXRD), thermal analysis and FTIR spectroscopy. The clopidogrel hydrogensulfate Form IV of the present invention is characterized by a PXRD pattern (FIG. 6) with peaks at about 22.0, 25.9, 26.9, 27.4, 28.1, 28.6 and 28.9±0.2 degrees two theta. More particularly, clopidogrel hydrogensulfate Form IV is characterized by a PXRD pattern with peaks at about 11.0, 12.5, 13.3, 14.0, 17.6, 18.2, 18.8, 20.5, 22.0, 22.9, 24.1, 25.9, 26.9, 27.4, 28.1, 28.6 and 28.9±0.2 degrees two theta.

Figure 7:
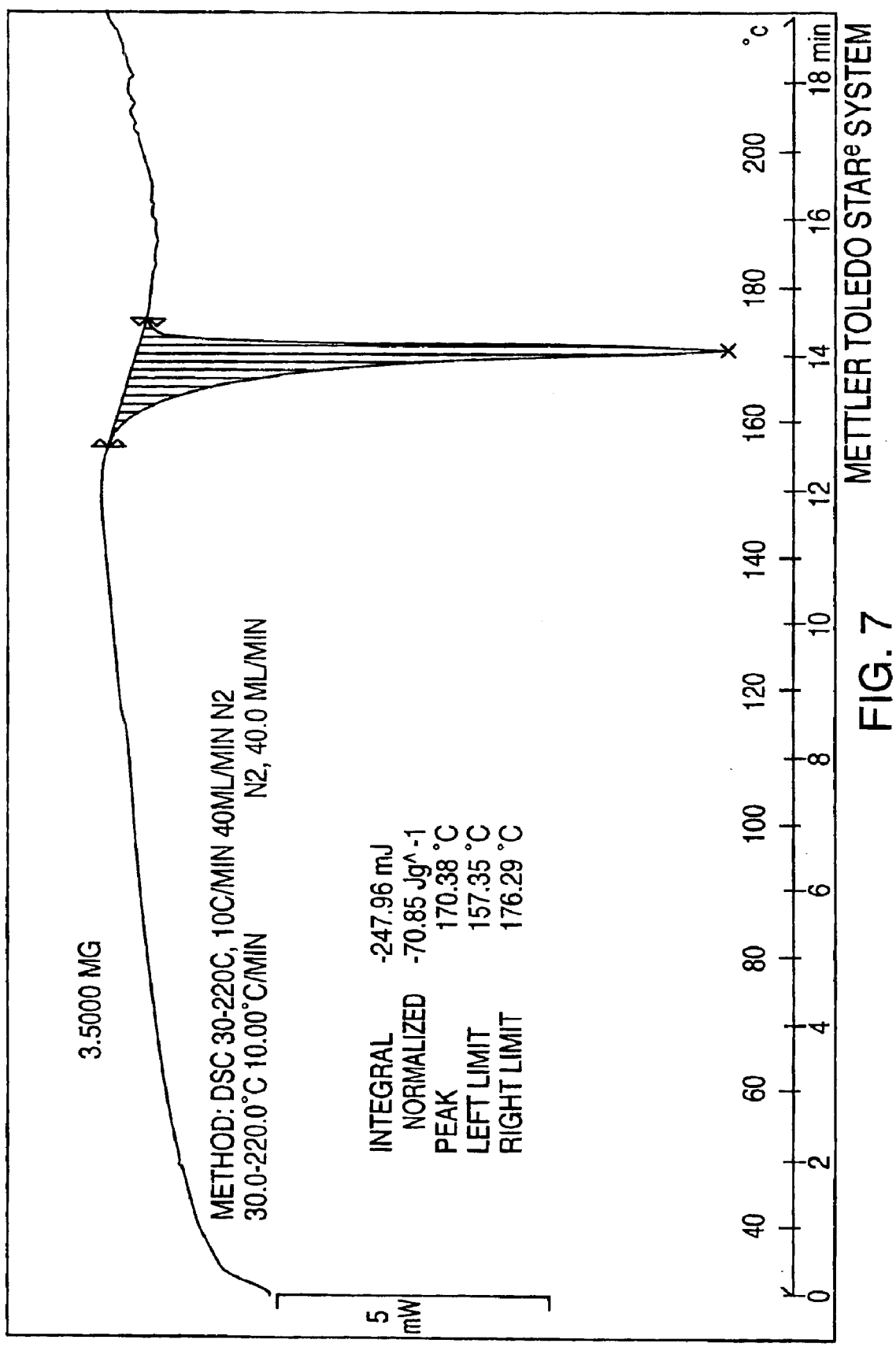
FIG. 7 is a DSC thermogram of clopidogrel hydrogensulfate Form IV.
Figure 8:
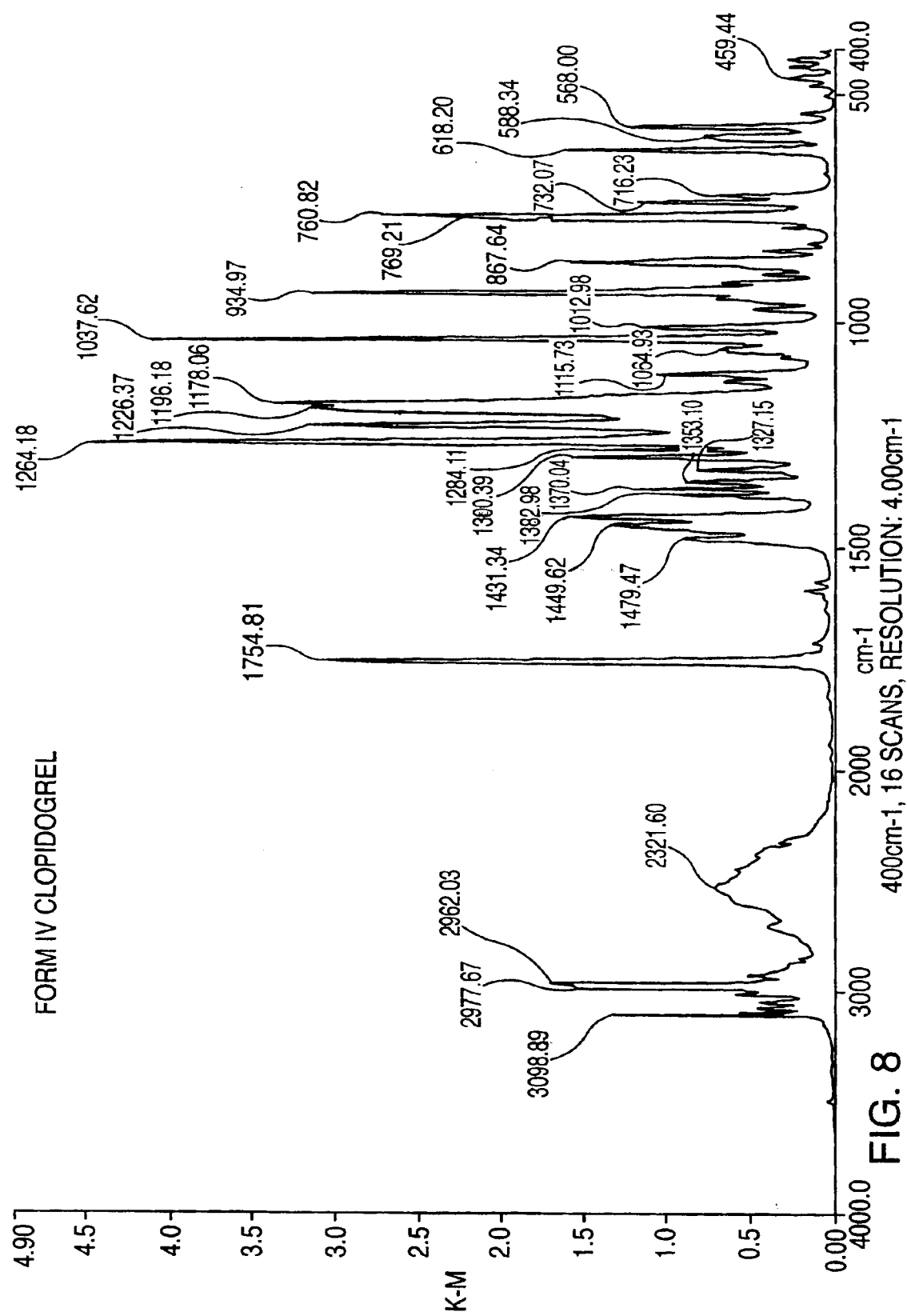
FIG. 8 is a FTIR spectrum of clopidogrel hydrogensulfate Form IV.

Clopidogrel hydrogensulfate Form IV is also characterized by DSC. The DSC thermogram of clopidogrel hydrogensulfate Form IV (FIG. 7) is characterized by an endothermic peak at about 160–170° C. Clopidogrel hydrogensulfate Form IV is also characterized by a FTIR spectrum (FIG. 8) with peaks at about 618, 769, 842, 893, 935, 974, 1038, 1116, 1370, 1384 $cm^{-1}$.

The present invention provides a process for preparing clopidogrel hydrogensulfate Form IV comprising the steps of preparing a solution of clopidogrel hydrogensulfate in isopropanol, precipitating clopidogrel hydrogensulfate and separating the clopidogrel hydrogensulfate.

Clopidogrel hydrogensulfate is dissolved in isopropanol to form a solution. Preferably, the isopropanol is heated to about reflux, before the addition of the clopidogrel hydrogensulfate, to make the isopropanol substantially soluble for the clopidogrel hydrogensulfate. The resulting solution is then cooled to about room temperature. One skilled in the art appreciates that other conditions and temperatures may have the same result.

In one embodiment, the cooled solution is allowed to sit at room temperature until precipitation occurs. The solution may optionally be stirred. After stirring for a few hours, precipitation occurs, and is subsequently separated. The precipitate may be separated according to methods well known in the prior art, such as by filtering, decanting and centrifugation, filtering being the most preferred method.

After separating the precipitate, it may optionally be dried. To dry, the precipitate may be heated, or the pressure reduced to accelerate the drying process. Preferably, a vacuum oven is used to heat the precipitate for about 16 hours at a temperature of about 50° C. The result of this process is clopidogrel hydrogensulfate Form IV.

In another embodiment, after cooling the solution, the solvent is removed to leave a dry residue. The solvent is preferably removed by evaporation. The pressure may be reduced to accelerate the drying process. Analysis of the residue confirmed that it is clopidogrel hydrogensulfate Form IV. With this embodiment, a subsequent separation and drying step is not necessary since the obtained residue is already dry and separated from the solvent. The process for preparation of Form IV does not require an additional step of using an anti solvent.

The present invention also provides for clopidogrel hydrogensulfate Form V. Clopidogrel hydrogensulfate Form V is characterized by PXRD, thermal analysis and by FTIR spectroscopy.

Figure 9:
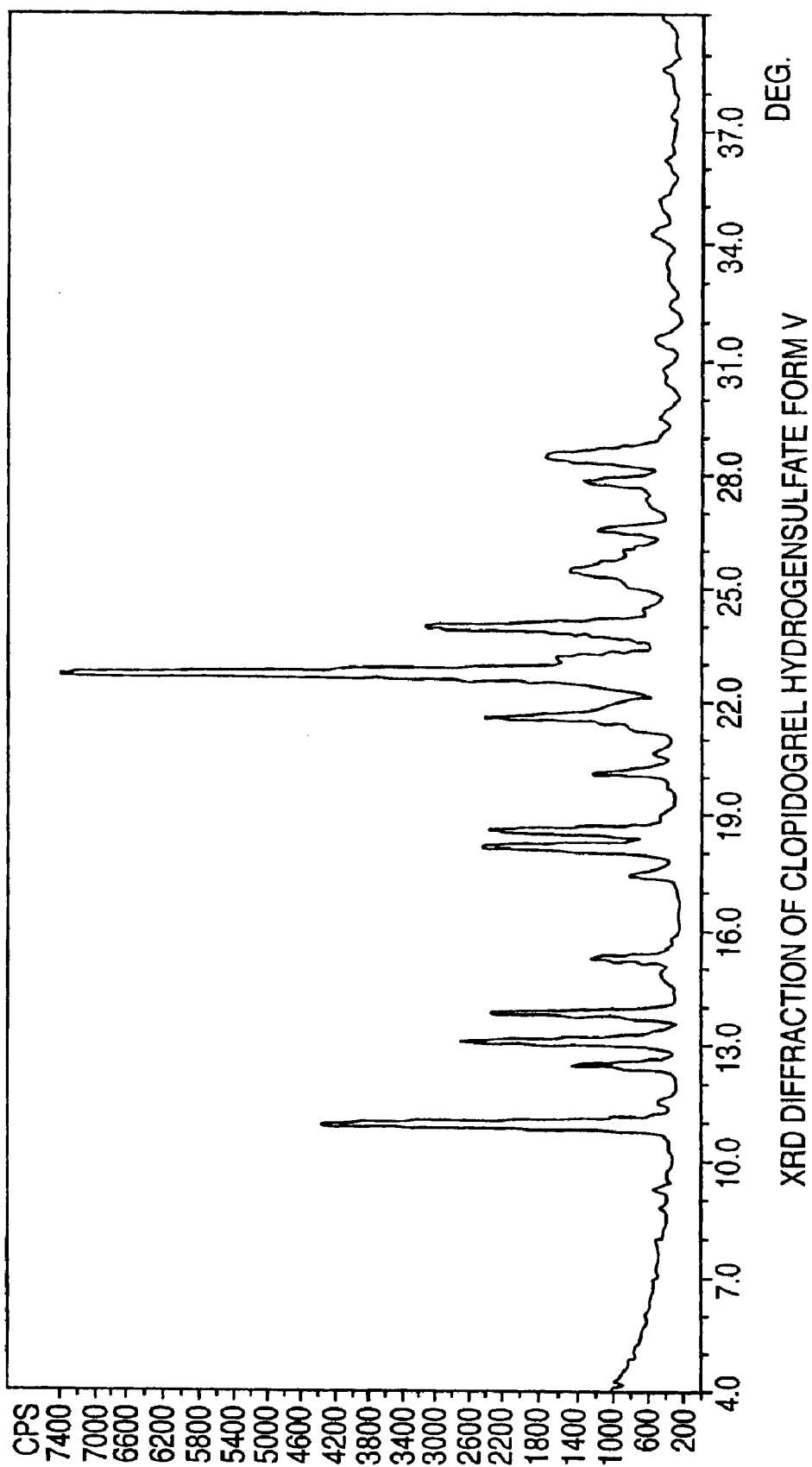
FIG. 9 is a PXRD pattern of clopidogrel hydrogensulfate Form V.

Clopidogrel hydrogensulfate Form V is characterized a PXRD diffraction pattern (FIG. 9) with peaks at about 25.5, 26.6, 27.8 and 28.5±0.2 degrees two theta. Clopidogrel hydrogensulfate Form V is particularly characterized by a PXRD diffraction pattern with peaks at about 11.0, 12.4, 13.1, 13.8, 15.2, 17.5, 18.1, 18.6, 20.2, 21.6, 22.7, 24.0, 25.5, 26.6, 27.8 and 28.5±0.2 degrees two theta.

Figure 10:
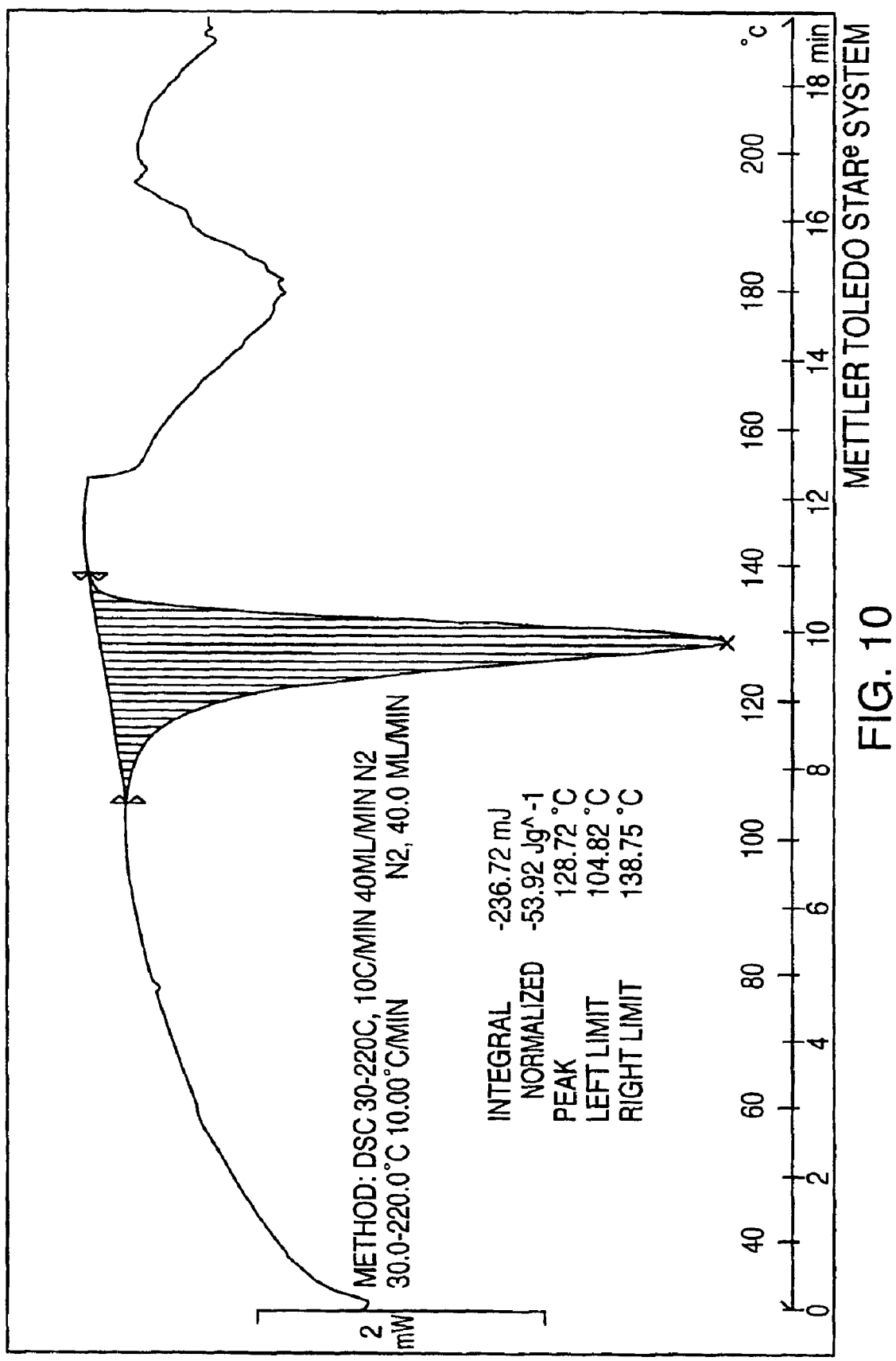
FIG. 10 is a DSC thermogram of clopidogrel hydrogensulfate Form V.
Figure 11:
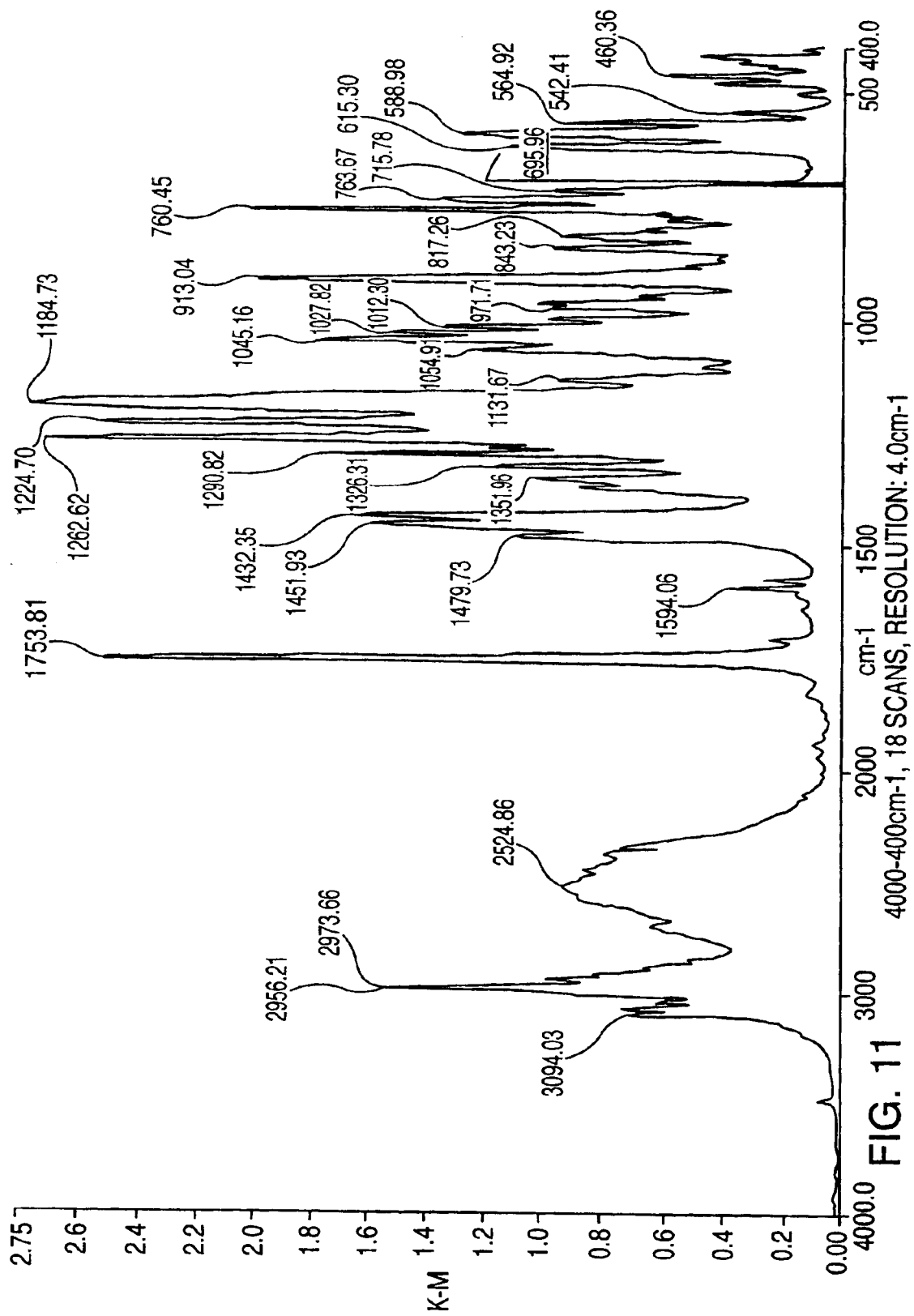
FIG. 11 is a FTIR spectrum of clopidogrel hydrogensulfate Form V.

Clopidogrel hydrogensulfate Form V is characterized by Differential Scanning Calorimetry (DSC) (10° C./min, Nitrogen atmosphere). DSC profile of clopidogrel hydrogensulfate Form V (FIG. 10) is characterized by a sharp endothermic peak at about 126–132° C. Clopidogrel hydrogensulfate Form V is also characterized by a FTIR spectrum (FIG. 11) with peaks at about 623, 743, 802, 817, 843, 963, 972, 1028 and 1374 $cm^{-1}$.

The present invention provides a process for preparing clopidogrel Form V comprising the steps of dissolving clopidogrel hydrogensulfate in 2-butanol to form a solution, admixing an antisolvent with the solution to precipitate clopidogrel hydrogensulfate and separating the clopidogrel hydrogensulfate. Preferably, the antisolvent is added to the solution. The precipitate may optionally be dried. Preferably, the precipitate is dried under reduced pressure and at elevated temperature. Most preferably, the precipitate is dried in a vacuum oven for about 24 hours at a temperature of about 50° C.

First, clopidogrel hydrogensulfate is dissolved in 2-butanol. The solution may be heated to substantially dissolve the clopidogrel hydrogensulfate in the alcohol. Preferably, the solution is heated to about reflux.

After heating, the solution is cooled. In one embodiment, after cooling, the solvent is removed from the solution, preferably by evaporation under reduced pressure, to obtain a residue. An antisolvent is then added to the residue.

In another embodiment, after cooling the solution, the antisolvent is added to the solution without the removal of the solvent. The antisolvent is preferably added slowly, such as dropwise.

Preferably, the antisolvent is an ether. More preferably, each alkyl radical of the ether is independently selected from the group consisting of methyl, ethyl, propyl, isopropyl, butyl, 1-butyl, 2-butyl and t-butyl. Most preferably, the ether is diethyl ether or methyl-t-butylether.

After addition of the antisolvent, a precipitate forms. The solution or the suspension is optionally stirred from about a few hours to about several days. The precipitate is then separated. The precipitate may be separated by methods well known in the art, such as filtering.

After separation, the precipitate may optionally be washed with an organic solvent, such as an ether. The precipitate may then be dried. The pressure may be reduced or the temperature raised to accelerate the drying process. Preferably, the precipitate is dried in a vacuum oven at a temperature of about 40° C. to 70° C. for about 24 hours.

Figure 12:
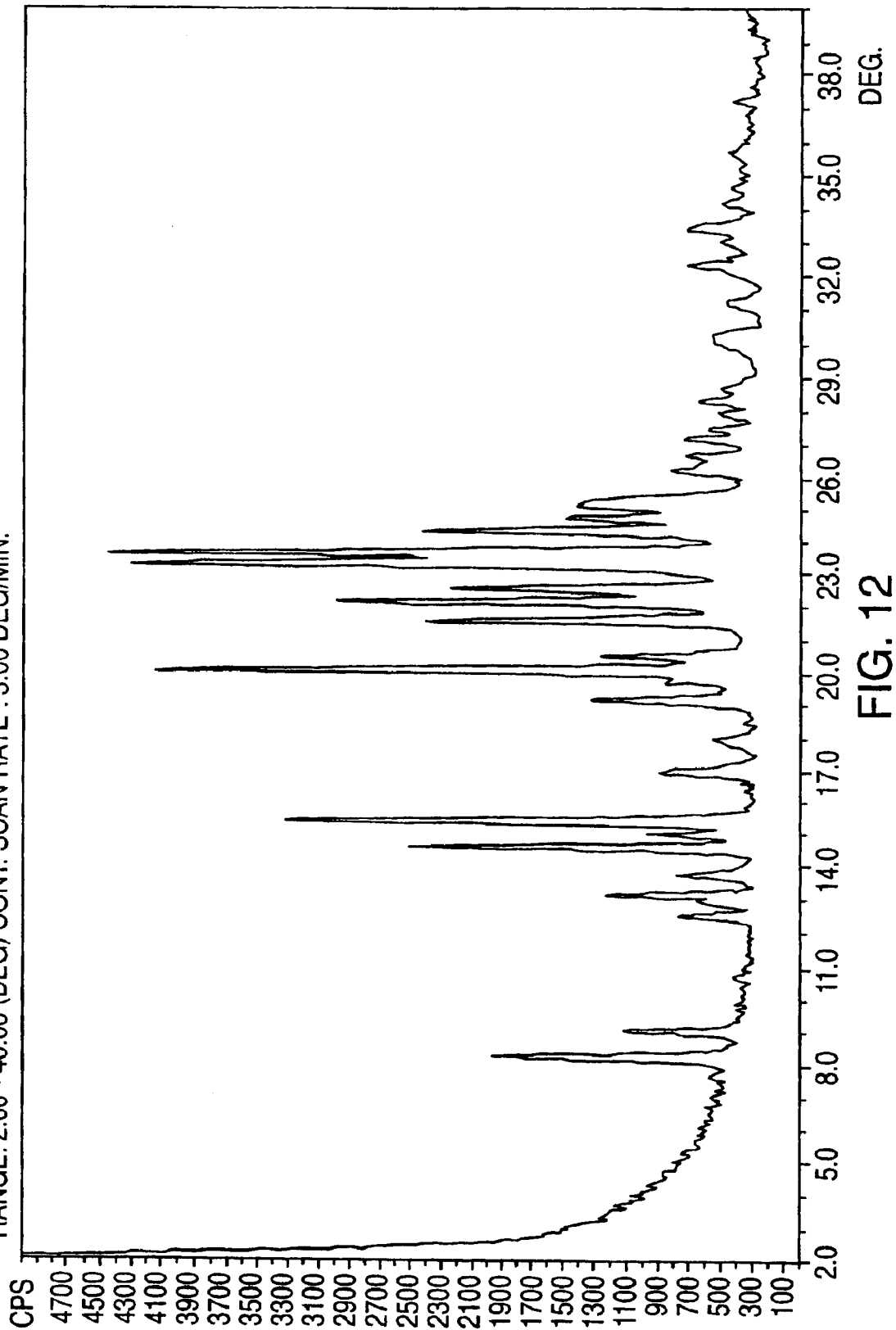
FIG. 12 is a PXRD pattern of clopidogrel hydrogensulfate Form VI.

The present invention also provides for clopidogrel hydrogensulfate Form VI. Clopidogrel hydrogensulfate is characterized by a PXRD pattern (FIG. 12) with peaks at about 8.3, 9.1, 23.2, 23.6±0.2 degrees two theta. More particularly, clopidogrel hydrogensulfate Form VI is characterized by a PXRD pattern with peaks at about 12.6, 13.2, 13.8, 14.7, 15.0, 15.4, 19.1, 20.0, 20.4, 21.5, 22.1, 22.5, 24.3, 24.7 and 25.1±0.2 degrees two theta.

Figure 13:
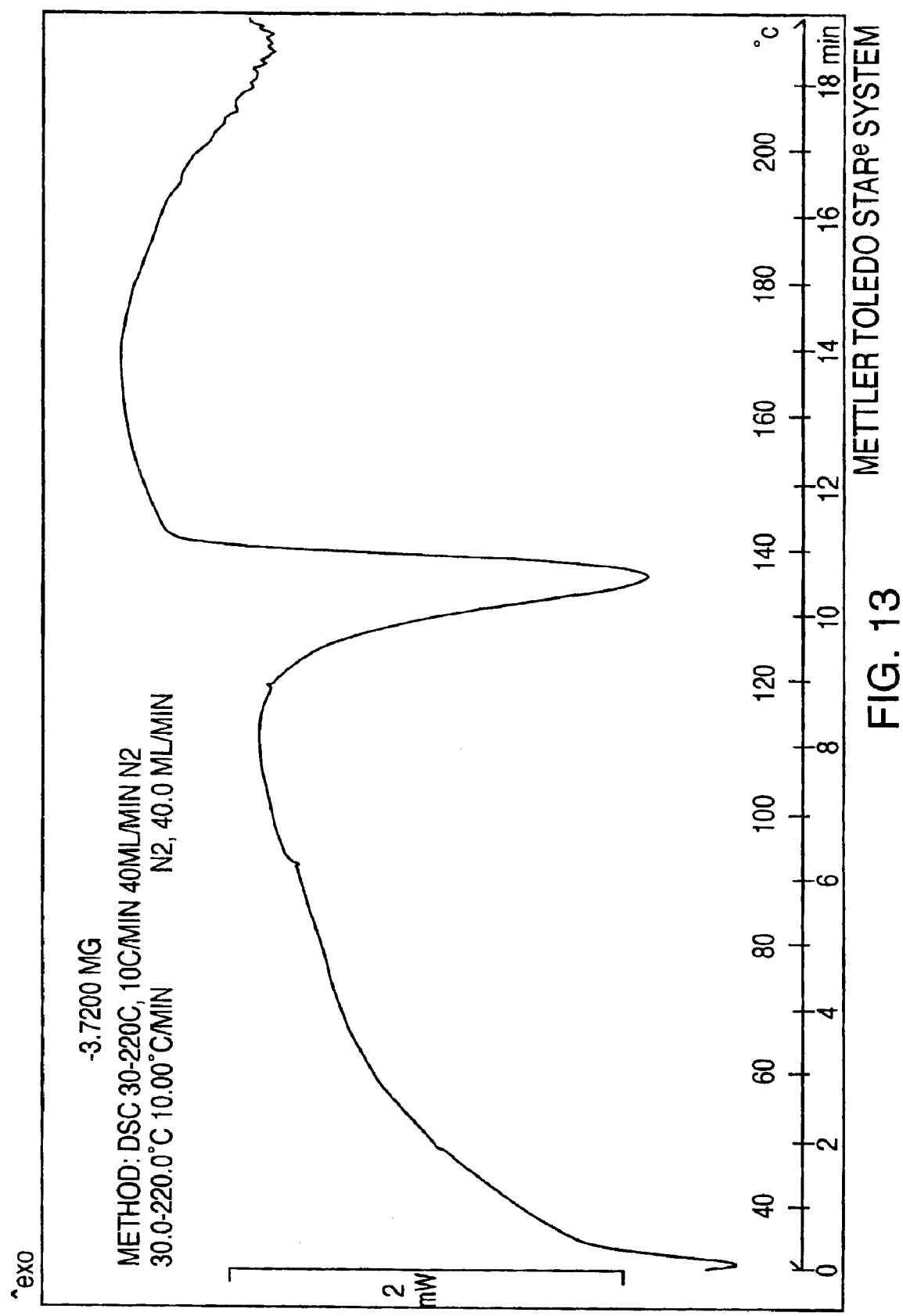
FIG. 13 is a DSC thermogram of clopidogrel hydrogensulfate Form VI.

Clopidogrel hydrogensulfate Form VI is also characterized by a DSC thermogram (FIG. 13) with an endothermic peak at about 136° C.

Figure 14:
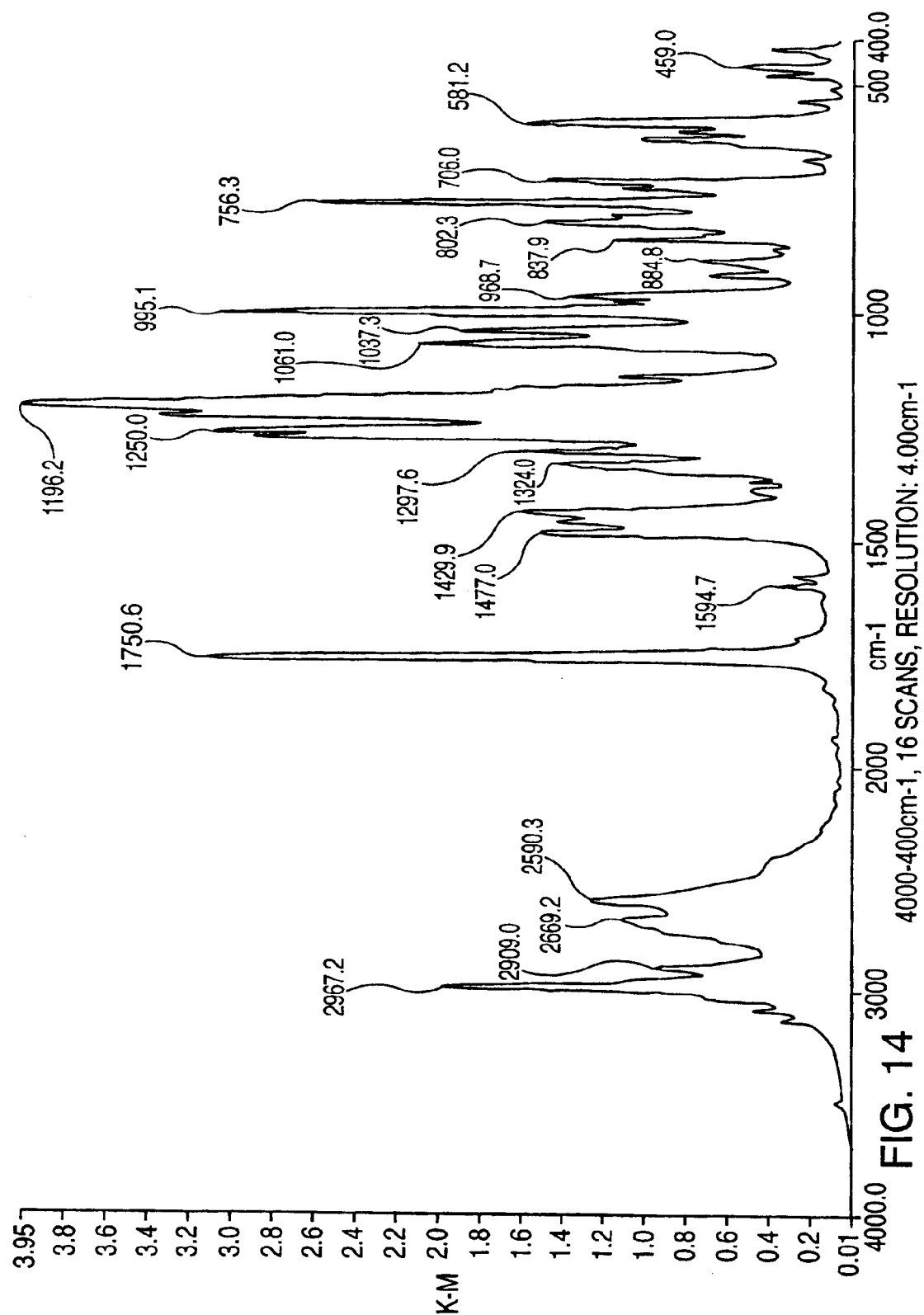
FIG. 14 is a FTIR spectrum of clopidogrel hydrogensulfate Form VI.

Clopidogrel hydrogensulfate Form VI is also characterized by a FTIR spectrum (FIG. 14) with peaks at about 959, 1061, 1430, 1751, 1757 and 3118 $cm^{-1}$.

The present invention also provides for a process for preparing clopidogrel hydrogensulfate Form VI comprising the steps of preparing a solution of clopidogrel hydrogensulfate in 1-propanol, removing the 1-propanol from the solution to obtain a residue, admixing an antisolvent with the residue to precipitate clopidogrel hydrogensulfate and separating the precipitate.

Clopidogrel hydrogensulfate is dissolved in 1-propanol to obtain a solution. The solution may be heated to substantially dissolve the clopidogrel hydrogensulfate in 1-propanol. Preferably, the solution is heated to about reflux for a few hours.

After heating, the solution is preferably cooled to about room temperature and stirred. The solvent is then removed, preferably by evaporation. To accelerate the evaporation process, the pressure may be reduced. Preferably, the solvent is completely evaporated to obtain an oily residue.

An antisolvent is then added to the residue. Preferably, the antisolvent is an ether. More preferably, each alkyl radical of the ether is independently selected from the group consisting of methyl, ethyl, propyl, isopropyl, butyl, 1-butyl, 2-butyl and t-butyl. Most preferably, the ether is methyl t-butylether.

The antisolvent is added to the residue, and the resulting mixture is preferably stirred for a day. A precipitate starts to form, which may be separated by methods well known in the art, such as filtration.

The precipitate is preferably dried. The precipitate may be heated or the pressure reduced to accelerate the drying process. Preferably the precipitate is heated from about 40° C. to about 60° C., with about 50° C. being the most preferred. A vacuum oven known in the art may be used for about one or two days to dry the precipitate.

The present invention further provides a process for preparing clopidogrel hydrogensulfate Form II comprising the steps of preparing a solution of clopidogrel hydrogensulfate in a solvent selected from the group consisting of chloroform, dichloromethane, 1,4-dioxane, toluene, ethyl acetate, methylethyl ketone and t-butylmethyl ether, precipitating clopidogrel hydrogensulfate from the solution, and separating the clopidogrel hydrogensulfate.

As the examples illustrate, one skilled in the art would appreciate that the optimal conditions for crystallizing clopidogrel hydrogensulfate Form II from these solvents is solvent dependent. The conditions used for crystallization may vary from one solvent to another.

Typically, clopidogrel hydrogensulfate is dissolved in one of the solvents and is preferably heated to obtain a complete solution. Preferably the solution is heated for about a few hours.

After dissolution, the solution is cooled. Preferably, the solution is cooled to about room temperature. The solutions may precipitate under slightly different conditions depending on the solvent used. The solution may be concentrated by partially removing the solvent, such as by evaporation. The solution may be stirred from about a few hours to about a few days. After precipitation, the precipitate may be separated by techniques well known in the art, such as by filtration.

Preferably the precipitate is dried. The precipitate may be heated or the pressure reduced to accelerate the drying process. Preferably the precipitate is heated from about 40° C. to about 60° C., with about 50° C. being the most preferred. A vacuum oven known in the art may be used for about one or two days to dry the precipitate.

The present invention further provides a process for preparing clopidogrel hydrogensulfate Form II comprising the steps of preparing a solution of clopidogrel hydrogensulfate in acetonitrile, admixing the solution with an antisolvent to precipitate clopidogrel hydrogensulfate and separating the clopidogrel hydrogensulfate. Preferably, the solution is added to the antisolvent.

Preferably, the solution is prepared by mixing amorphous clopidogrel hydrogensulfate with acetonitrile. Preferably the solution is kept at about room temperature. The solution is then added to an antisolvent to precipitate clopidogrel hydrogensulfate. Preferably, the solution is added slowly to the antisolvent.

The antisolvent is preferably an ether. More preferably, each alkyl radical of the ether is independently selected from the group consisting of methyl, ethyl, propyl, isopropyl, butyl, 1-butyl, 2-butyl and t-butyl. Most preferably, the ether is diethyl ether.

After addition of the solution to an antisolvent, a precipitate forms. The suspension may be stirred, preferably for about a day. The precipitate is then separated by techniques well known in the art, such as by filtration.

Preferably the precipitate is dried. The precipitate may be heated or the pressure reduced to accelerate the drying process. Preferably the precipitate is heated from about 50° C. to about 70° C., with about 65° C. being the most preferred. A vacuum oven known in the art may be used.

The new crystalline forms of clopidogrel hydrogensulfate are solvates of various solvents. Clopidogrel hydrogensulfate Form III is a solvate of 1-butanol. Form IV is considered a solvate of ispropanol. Form V is a solvate of 2-butanol. Form VI is a solvate of 1-propanol.

Clopidogrel hydrogensulfate Form III contains about 7 to about 8% 1-butanol by weight. Form IV contains about 3% to about 9% isopropanol by weight. Form V contains about 9% to about 10% 2-butanol by weight. Form VI contains about 6% 1-propanol by weight.

One skilled in the art may appreciate that the processes of the present invention may use clopidogrel free base rather than clopidogrel hydrogensulfate as a starting material. After preparing a solution of an alcohol and the free base, the free base may be treated with sulfuric acid to obtain the hydrogensulfate form. The solution is then preferably heated to reflux for a few hours. Preferably, the sulfuric acid used is about 20% to about 98% aqueous sulfuric acid, most preferably about 80% aqueous sulfuric acid. The molar equivalent of sulfuric acid to clopidogrel base used is preferably from about 0.66 equivalents to about 1.1 equivalents.

One skilled in the art would appreciate that the conditions and the yield may vary when starting with clopidogrel base rather than clopidogrel hydrogensulfate.

The yield and the conditions may further vary according to the molar ratio and the concentration of the sulfuric acid used The examples of the present invention provide guidance to one skilled in the art regarding the optimal conditions.

One skilled in the art may also appreciate that the scope of the disclosure is not limited by the order of the additions in adding an antisolvent. For example, a mixture may be added to an antisolvent or vice versa, though an embodiment may prefer one over the other. Usually the crystallization of clopidogrel is better when a solution is added to the antisolvent, but operationally it is often more convenient to add the antisolvent to the solution. When adding an antisolvent to a residue, the order of addition is of minimal relevance.

One of skill in the art appreciates the use of an anti-solvent to cause precipitation of a compound. In one embodiment, an anti-solvent is added to a solution to decrease the solubility for a particular compound in a particular solvent, thus resulting in precipitation. In another embodiment, an anti-solvent is added to an oily residue or a gummy material, wherein the low solubility of the anti-solvent for a particular compound results in precipitation of that compound.

Many processes of the present invention involve crystallization out of a particular solvent. One skilled in the art would appreciate that the conditions concerning crystallization can be modified without affecting the form of the polymorph obtained. For example, when mixing clopidogrel hydrogensulfate in a solvent to form a solution, warming of the mixture can be necessary to completely dissolve the starting material. If warming does not clarify the mixture, the mixture can be diluted or filtered. To filter, the hot mixture can be passed through paper, glass fiber or other membrane material, or a clarifying agent such as celite. Depending upon the equipment used and the concentration and temperature of the solution, the filtration apparatus may need to be preheated to avoid premature crystallization.

The conditions can also be changed to induce/accelerate precipitation. A preferred way of inducing precipitation is to reduce the solubility of the solvent. The solubility of the solvent can be reduced, for example, by cooling the solvent.

Another manner to accelerate crystallization is by seeding with a crystal of the product or scratching the inner surface of the crystallization vessel with a glass rod. Other times, crystallization can occur spontaneously without any inducement. The present invention covers both embodiments where crystallization or precipitation occurs spontaneously, or is induced/accelerated, unless if such inducement is critical for obtaining a particular polymorph.

As a platelet inhibitor, clopidogrel is effective at suppressing the lethal effects of blood clotting. Platelet aggregation often occurs around damaged blood vessels. The blood vessels may only have minor fissures or plaques to induce platelet aggregation.

Platelet aggregation leads to the blockage of arteries, thus increasing the risk of primary and secondary strokes and heart attacks. By inhibiting platelet aggregation, clopidogrel hydrogensulfate reduces the risk of heart attacks and strokes. Clopidogrel is particularly effective in the secondary prevention of ischemic events, which are defined in the art as a decrease in the blood supply to a bodily organ, tissue, or part caused by constriction or obstruction of the blood vessels.

Pharmaceutical compositions of the present invention contain clopidogrel hydrogensulfate Forms III, IV, V, VI and the amorphous form, optionally in mixture with other Form(s) or amorphous clopidogrel and/or active ingredients. The clopidogrel hydrogensulfate Forms III, IV, V and VI obtained by the processes of the present invention are ideal for pharmaceutical composition in that they have a purity of at least about 90%, more preferably at least about 95%, and most preferably at least about 99%. (Area percentage as measured by HPLC). In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, clopidogrel hydrogensulfate and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granulate. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Capsules, tablets and lozenges, and other unit dosage forms preferably contain a base equivalent of about 75 mg, which is about 98 grams of clopidogrel hydrogensulfate Form III, IV, V, VI or the amorphous form. The unit dosage form as used herein refers to the amount of the various forms of clopidogrel contained in the vehicle of administration, such as a tablet or a capsule. In a preferred embodiment, the unit dosage in a tablet for oral administration contains a base equivalent of about 25 mg to 150 mg. Most preferably, it is about 75 mg base equivalent. One skilled in the art would appreciate that other unit dosages may be made as necessary in a routine fashion.

Instruments Used:
PXRD

Powder X-ray diffraction patterns were obtained by methods known in the art using a Scintag X-ray powder diffractometer model X'TRA, a variable goniometer, an X-Ray tube with Cu target anode and a solid state detector. A round standard aluminum sample holder with a round zero background quartz plate was used. Scans were performed over a range of 2 to 40 degrees two-theta, continuously, with a scan rate of 3 degrees/min.

DSC

The DSC thermogram was obtained using a DSC Mettler 821e Stare. The temperature range of scans was 30–350° C. at a rate of 10° C./min. The weight of the sample was 3–5 mg. The sample was purged with nitrogen gas at a flow rate of 40 mL/min. Standard 40 µl aluminum crucibles having lids with three small holes were used.

FTIR

To obtain the FTIR results, a Perkin-Elmer Spectrum One FTIR spectrometer with the diffuse reflectance technique was used. The sample was finely ground with potassium bromide, and the spectrum was recorded using potassium bromide background in a diffused reflectance accessory. The spectrum was recorded from 4000–400 cm$^{-1}$. Sixteen scans were taken at a resolution of 4.0 cm$^{-1}$.

For FTIR, KBr tablets were not used. In the prior art, Form II was characterized by FTIR using KBr tablets. As disclosed, Applicants performed FTIR by diffuse reflectance technique ("DRIFT"). Clopidogrel hydrogensulfate Form I and Form II were analyzed both by DRIFT technique and by KBr tablet technique. Similar pattern were obtained for the same crystal form by the different techniques.

HPLC
Column and Packing: Keystone, Betasil C 18, 250×4.6
Eluent: 70% methanol, 30% buffer 10.01M K2HP04, pH=7.5 with H$_3$PO$_4$
Flow Rate: 1 ml/min
Column Temp: 30° C.
Detection wavelength=230 nm
Diluent: 70% methanol/30% water
Sample: 10 mg/10 ml diluent
Injection volume: 20 micro liters, Instrument: Varian The following examples further illustrate the present invention:

EXAMPLES

Example 1

Preparation of Clopidogrel Hydrogensulfate Form II

Clopidogrel base (5.01 g, leq.) was dissolved in methylethyl ketone (MEK) (39.5 mL). Eighty percent aqueous sulfuric acid (0.74 mL, 0.66 eq.) was added to the solution at 20° C. The reaction mixture was heated to reflux temperature for 2 hours. Then, the solution was cooled to room temperature and half of the amount of the solvent was evaporated under reduced pressure during which a precipitate was formed. The white solid was collected by filtration, washed with MEK (2×10 ml) and dried at 50° C. in a vacuum oven for 24 hours to obtain 3.55 g (54%) of clopidogrel hydrogensulfate crystal Form II.

Example 2

Preparation of Clopidogrel Hydrogensulfate Form II

Clopidogrel base (4.27 g, 1 eq.) was dissolved in methylethyl ketone (MEK) (33.7 ml). Eighty percent aqueous sulfuric acid (1.03 ml, 1.1 eq.) was added to the solution at 20° C. The reaction mixture was heated to reflux temperature for 2 hours. Then, the solution was cooled to room temperature and stirred at this temperature for additional 67 hours during which a precipitate was formed. The white solid was collected by filtration, washed with MEK (2×10 mL) and dried at 50° C. in a vacuum oven for 24 hours to obtain 4.59 g (82%) of clopidogrel hydrogensulfate crystal Form II.

Example 3

Preparation of Clopidogrel Hydrogensulfate Form II

Clopidogrel base (3.73 g, leq.) was dissolved in dichloromethane (29.4 mL). Eighty percent aqueous sulfuric acid (0.55 ml, 0.66 eq.) was added to the solution at 20° C. The reaction mixture was heated to reflux temperature for 2 hours during which a precipitate was formed. Then, the solution was cooled to room temperature and half of the amount of the solvent was evaporated under reduced pressure. The white solid was collected by filtration, washed with dichloromethane (2×10 ml) and dried at 50° C. in a vacuum oven for 24 hours to obtain 1.42 g (30%) of clopidogrel hydrogensulfate crystal Form I.

Example 4

Preparation of Clopidogrel Hydrogensulfate Form II

Clopidogrel base (4.37 g, 1 eq.) was dissolved in dichloromethane (34.5 mL). Eighty percent aqueous sulfuric acid (1.06 mL, 1.1 eq.) was added to the solution at 20° C. The reaction mixture was heated to reflux temperature for 2 hours during which a turbid solution was formed. Then, the solution was cooled to room temperature and stirred at this temperature for an additional 16 hours during which a massive precipitate was formed. The white solid was collected by filtration, washed with dichloromethane (2×10 ml) and dried at 50° C. in a vacuum oven for 24 hours to obtain 2.76 g (48%) of clopidogrel hydrogensulfate crystal Form II.

Example 5

Preparation of Clopidogrel Hydrogensulfate Form II

Clopidogrel base (4.29 g, 1 eq.) was dissolved in toluene (33.8 mL). Eighty percent aqueous sulfuric acid (1.04 mL, 1.1 eq.) was added to the solution at 20° C. The reaction mixture was heated to reflux temperature for 3 hours. Then, the solution was cooled to room temperature and stirred at this temperature for an additional 16 hours during which a massive precipitate was formed. The white solid was collected by filtration, washed with toluene (2×10 ml) and dried at 50° C. in a vacuum oven for 24 hours to obtain 4.59 g (82%) of clopidogrel hydrogensulfate crystal Form II.

Example 6

Preparation of Clopidogrel Hydrogensulfate Form II

Clopidogrel base (4.24 g, leq.) was dissolved in chloroform (33.4 mL). Eighty percent aqueous sulfuric acid (0.62 mL, 0.66 eq.) was added to the solution at 20° C. The reaction mixture was heated to reflux temperature for 2 hours during which a precipitate was formed. Then, the solution was cooled to room temperature and half of the amount of the solvent was evaporated under reduced pressure. The white solid was collected by filtration, washed with chloroform (2×10 mL) and dried at 50° C. in a vacuum oven for 24 hours to obtain 3.14 g (56%) of clopidogrel hydrogensulfate crystal Form II.

Example 7

Preparation of Clopidogrel Hydrogensulfate Form II

Clopidogrel base (4.37 g, leq.) was dissolved in chloroform (34.5 mL). Eighty percent aqueous sulfuric acid (1.06 ml, 1.1 eq.) was added to the solution at 20° C. The reaction mixture was heated to reflux temperature for 2 hours during which a precipitate was formed. Then, the solution was cooled to room temperature and stirred at this temperature for an additional 16 hours during which a massive precipitate was formed. The white solid was collected by filtration, washed with chloroform (2×10 ml) and dried at 50° C. in a vacuum oven for 24 hours to obtain 5.01 g (88%) of Clopidogrel hydrogensulfate crystal Form II.

Example 8

Preparation of Clopidogrel Hydrogensulfate Form II

Clopidogrel base (4.03 g, 1 eq.) was dissolved in ethyl acetate (31.8 mL). Eighty percent aqueous sulfuric acid (0.59 mL, 0.66 eq.) was added to the solution at 20° C. The reaction mixture was heated to reflux temperature for 3 hours during which a sticky precipitate was formed. Then, the solution was cooled to room temperature and stirred at this temperature for an additional 16 hours during which a massive precipitate was formed. The white solid was collected by filtration, washed with ethyl acetate (2×10 ml) and dried at 50° C. in a vacuum oven for 24 hours to obtain 2.59 g (49%) of clopidogrel hydrogensulfate crystal Form II.

Example 9

Preparation of Clopidogrel Hydrogensulfate Form II

Clopidogrel base (5.31 g, leq.) was dissolved in ethyl acetate (41.9 mL). Eighty percent aqueous sulfuric acid (1.29 mL, 1.1 eq.) was added to the solution at 20° C. The reaction mixture was heated to reflux temperature for 2 hours during which a massive precipitate was formed. Then, the solution was cooled to room temperature and stirred at this temperature for an additional 3 hours. The white solid was collected by filtration, washed with ethyl acetate (2×10 ml) and dried at 50° C. in a vacuum oven for 24 hours to obtain 4.60 g (66%) of clopidogrel hydrogensulfate crystal Form II.

Example 10

Preparation of Clopidogrel Hydrogensulfate Form II

Clopidogrel base (4.39 g, leq.) was dissolved in tert-butylmethyl ether (MTBE) (34.6 ml). Eighty percent aqueous sulfuric acid (0.64 ml, 0.66 eq.) was added to the solution at 20° C. The reaction mixture was heated to reflux temperature for 3 hours during which a sticky precipitate was formed. Then, the solution was cooled to room temperature and stirred at this temperature for an additional 2 hours. The obtained white solid was collected by filtration, washed with MTBE (2×10 mL) and dried at 50° C. in a vacuum oven for 24 hours to obtain 2.96 g (52%) of clopidogrel hydrogensulfate crystal Form II.

Example 11

Preparation of Clopidogrel Hydrogensulfate Form II

Clopidogrel base (4.17 g, leq.) was dissolved in 1,4-Dioxane (32.9 mL). Eighty percent aqueous sulfuric acid (0.61 ml, 0.66 eq.) was added to the solution at 20° C. The reaction mixture was heated to reflux temperature for 2 hours during which a massive precipitate was formed. Then, the solution was cooled to room temperature and stirred at this temperature for additional 2 hours. The white solid was collected by filtration, washed with 1,4-dioxane (2×10 mL) and dried at 50° C. in a vacuum oven for 24 hours to obtain 2.61 g (48%) of clopidogrel hydrogensulfate crystal Form II.

Example 12

Preparation of Clopidogrel Hydrogensulfate Form II

Amorphous clopidogrel hydrogensulfate (1 g) was dissolved in acetonitrile (6 mL) at room temperature. The resulting solution was added to DEE (350 ml) drop wise and the obtained suspension was stirred at room temperature for 19 hours. The white solid was collected by filtration, washed with DEE (15 mL) and dried at 65° C. in a vacuum oven for 24 hours to obtain 0.71 g (71%) of clopidogrel hydrogensulfate crystal Form II.

Example 13

Preparation of Clopidogrel Hydrogensulfate Amorphous Form

Clopidogrel hydrogensulfate (3 grams) was dissolved in methanol (6 mL). Toluene (350 mL) was separately heated to reflux temperature. The methanolic solution of clopidogrel hydrogensulfate was added dropwise to the boiling toluene. The resulting solution was refluxed for an additional 20 minutes. The solution was cooled to room temperature and was stirred at this temperature for 16 hours. The solvent was evaporated under reduced pressure to dryness to obtain a creamy foam (1.26 grams, 42%), which characterization data showed to be the amorphous form.

Example 14

Preparation of Clopidogrel Hydrogensulfate Amorphous Form

Clopidogrel hydrogensulfate (2 grams) was dissolved in methanol (4 mL). The resulting solution was added dropwise to diethyl ether (350 mL). The suspension was stirred at RT for about forty five minutes. The solid was filtered and dried at about 50° C. in a vacuum oven for 24 hours to give 1.12 grams (56%) of clopidogrel hydrogensulfate, which characterization data showed to be the amorphous form.

Example 15

Preparation of Clopidogrel Hydrogensulfate Amorphous Form

Clopidogrel hydrogensulfate (1 gram) was dissolved in methanol (3 mL) at room temperature. The resulting solution was added drop wise to diethylether (DEE) (350 mL). The obtained mixture was stirred at room temperature for 0.5 hour. The solid was then filtered and dried at 50° C. in a vacuum oven for 16 hours to give 0.86 g (86%) of amorphous clopidogrel hydrogensulfate.

Example 16

Preparation of Clopidogrel Hydrogensulfate Amorphous Form

Clopidogrel base (3.42 g) was dissolved in acetone (27 mL). Aqueous sulfuric acid (20%, 4.57 mL) was added to the solution at 20° C. The reaction mixture was heated to reflux temperature for 2 hours. The solution was cooled to room temperature and stirred at this temperature for additional 1.5 hours. Then the solvent was evaporated to dryness under reduced pressure to obtain powder (3.59 g, 78%) which characterization data showed to be the amorphous form.

Example 17

Preparation of Clopidogrel Hydrogensulfate Amorphous Form

Clopidogrel base (2.88 g) was dissolved in acetone (23 mL). Aqueous sulfuric acid (20%, 2.56 mL) was added to the solution at 20° C. The reaction mixture was heated to reflux temperature for 2 hours. The solution was cooled to room temperature and stirred at this temperature for an additional 2 hours. Then the solvent was evaporated to dryness under reduced pressure to obtain powder (3.08 g, 82%) which characterization data showed to be the amorphous form.

Example 18

Preparation of Clopidogrel Hydrogensulfate Form I

Clopidogrel hydrogensulfate (2 grams) was dissolved in methanol (4 mL). The resulting solution was added to methyl t-butyl ether (300 mL) dropwise. The suspension was stirred at RT for 16 hours. The resulting precipitate was filtered and dried at 65° C. in a vacuum oven for 24 hours to obtain crystals (1.5 grams, 75%). Subsequent analysis confirmed that the crystals were clopidogrel hydrogensulfate Form I.

Example 19

Preparation of Clopidogrel Hydrogensulfate Form I

Clopidogrel hydrogensulfate (3 grams) was dissolved in absolute ethanol (9 mL) at reflux temperature to obtain a clear solution. The solution was then cooled to room temperature and the solvent was evaporated to dryness under reduced pressure to obtain oil. Then methyl t-butyl ether or diethylether (28 mL) were added dropwise to the oily residue and the resulting mixture was stirred at room temperature for 24 hours. The white product was filtered and dried at 50° C. in a vacuum oven for 24 hours to give 2.6 grams (87%) of clopidogrel hydrogensulfate crystal Form I.

Example 20

Preparation of Clopidogrel Hydrogensulfate Form I

Clopidogrel hydrogensulfate (3 grams) was dissolved in methanol (4 mL) at reflux temperature to obtain a clear solution. The solution was then cooled to room temperature and the solvent was evaporated to dryness under reduced pressure to obtain oil. Then tert-Butyl methylether or diethylether (30 mL) was added dropwise to the oily residue and the resulting mixture was stirred at room temperature for 16 hours. The white product was filtered and dried at 50° C. in a vacuum oven for 24 hours to give 2.65 grams (88%) of clopidogrel hydrogensulfate crystal Form I.

Example 21

Preparation of Clopidogrel Hydrogensulfate Form I and Amorphous Form

Clopidogrel base (3.85 g) was dissolved in absolute ethanol (30.4 mL). Eighty percent aqueous sulfuric acid (0.56 mL) was added to the solution. The reaction mixture was heated to reflex temperature for 2 hours. Then, the solution was cooled to room temperature and the solvent was evaporated to dryness under reduced pressure leaving a white foam. The foam was stirred in methyl t-butyl ether (MTBE) (70 ml) for 3 hours at room temperature. Approximately half of the MTBE was evaporated under reduced pressure and a solid was recovered by filtration. The solid was dried at 50° C. in a vacuum oven to obtain 2.82 g (56%) of a mixture of clopidogrel hydrogensulfate crystal Form I and amorphous clopidogrel hydrogensulfate.

Example 22

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 1 hour.

The solid was then filtered and dried at 50° C. in a vacuum oven for 19.5 hours to give 0.76 g (76%) of clopidogrel hydrogensulfate crystal Form I.

Example 23

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 5 hours. The solid was then filtered and dried at 50° C. in a vacuum oven for 14 hours to give 0.74 g (74%) of clopidogrel hydrogensulfate crystal Form I.

Example 24

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 8 hours. The solid was then filtered and dried at 50° C. in a vacuum oven for 13 hours to give 0.78 g (78%) of clopidogrel hydrogensulfate crystal Form I.

Example 25

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 19.5 hours. The solid was then filtered and dried at 50° C. in a vacuum oven for 23 hours to give 0.74 g (74%) of clopidogrel hydrogensulfate crystal Form I.

Example 26

Preparation of Clopidogrel Crystal Form III

A suspension of clopidogrel hydrogensulfate (3 grams) in 1-butanol (5 mL) was heated to reflux temperature for 30 minutes to obtain a clear solution. The solution was cooled to room temperature (RT) and the solvent was evaporated under reduced pressure to obtain an oily residue. Diethyl ether (30 mL) was added to the residue. The resulting mixture was stirred at room temperature for 24–48 hours. A white product precipitated from the mixture, and was then filtered, and washed with diethyl ether (2×10 mL). The white product was dried at 65° C. in a vacuum oven for 24 hours to give 2.91 grams of crystalline clopidogrel hydrogensulfate (97%), which was identified as Form III by PXRD.

Example 27

Preparation of Clopidogrel Crystal Form III

Clopidogrel base (4.28 g) was dissolved in 1-butanol (16.9 ml). Eighty percent aqueous sulfuric acid (0.63 ml) was added to the solution at 20° C. The reaction mixture was heated to reflux temperature for 2 hours. Then, the solution was cooled to room temperature and the solvent was evaporated to dryness under reduced pressure leaving yellow oil. The oil was stirred in methyl t-butyl ether (MTBE) (125 ml) for 96 hours at room temperature to obtain a precipitate. The solid was collected by filtration, washed with MTBE (2×10 ml) and dried at 50° C. in a vacuum oven for 24 hours to obtain 3.33 g (60%) of clopidogrel hydrogensulfate crystal Form III.

Example 28

Preparation of Clopidogrel Crystal Form III

Clopidogrel hydrogensulfate crystal Form I (1 g) was dissolved in 1-butanol (5 mL) at reflux temperature. When a clear solution was obtained, the solution was cooled to room temperature and the solvent was evaporated to dryness under reduced pressure to obtain an oily residue. Then diethyl ether (DEE) (7 mL) was added to the residue and the resulting mixture was stirred at room temperature for 24 hours during which a precipitate was formed. The white solid was collected by filtration, washed with DEE (25 mL) and dried at 60° C. in a vacuum oven for 20 hours to obtain 0.86 g (86%) of clopidogrel hydrogensulfate crystal Form III.

Example 29

Preparation of Clopidogrel Hydrogensulfate Form IV

Clopidogrel hydrogensulfate (3 grams) was dissolved in isopropanol (IPA) (32 mL (~11 vol.)) at reflux temperature. The resulting solution was cooled to room temperature and stirred at this temperature for 1 hour. The solid was then filtered and dried at 50° C. in a vacuum oven for 16 hours to give 1.66 g (55%) of clopidogrel hydrogensulfate crystal Form IV.

Remark: The volume of the solvent can be increased up to 21 volumes/1 g of clopidogrel hydrogensulfate.

Example 30

Preparation of Clopidogrel Hydrogensulfate Form IV

Clopidogrel hydrogensulfate (3 grams) was dissolved in isopropanol (IPA) (60 ml (20 vol.)) at reflux temperature. The resulting solution was cooled to room temperature and the solvent was evaporated to dryness under reduced pressure to give 2.0 g (67%) of clopidogrel hydrogensulfate crystal Form IV.

Example 31

Preparation of Clopidogrel Hydrogensulfate Form IV

Clopidogrel base (2.96 g) was dissolved in isopropanol (45 mL). Aqueous sulfuric acid (98%, 0.50 ml) was added to the solution at 20° C. The reaction mixture was heated to reflux temperature for 2 hours. Then, the solution was cooled to room temperature and stirred at this temperature for an additional 2 hours to obtain a white precipitate. The solid was collected by filtration, washed with isopropanol (2×10 ml) and dried at 50° C. in a vacuum oven for 28 hours to obtain 2.78 g (71%) of clopidogrel hydrogensulfate crystal Form IV.

Example 32

Preparation of Clopidogrel Hydrogensulfate Form IV

Clopidogrel base (2.91 g) was dissolved in isopropanol (IPA) (44 ml). Ninety eight percent aqueous sulfuric acid (0.32 ml) was added to the solution at 20° C. The reaction mixture was heated to reflux temperature for 2 hours. Then, the solution was cooled to room temperature and stirred at this temperature for an additional 2 hours to obtain a white precipitate. The solid was collected by filtration, washed with IPA (2×10 ml) and dried at 50° C. in a vacuum oven for 26 hours to obtain 3.04 g (80%) of clopidogrel hydrogensulfate crystal Form IV.

Example 33

Preparation of Clopidogrel Hydrogensulfate Form IV

Clopidogrel base (2.93 g) was dissolved in isopropanol (45 ml). Sixty percent aqueous sulfuric acid (0.99 mL) was added to the solution at 20° C. The reaction mixture was heated to reflux temperature for 2 hours. Then, the solution was cooled to room temperature and stirred at this temperature for an additional 2.5 hours to obtain a white precipitate. The solid was collected by filtration, washed with isopropanol (2×10 ml) and dried at 50° C. in a vacuum oven for 15 hours to obtain 2.22 g (58%) of clopidogrel hydrogensulfate crystal Form IV.

Example 34

Preparation of Clopidogrel Hydrogensulfate Form IV

Clopidogrel base (2.98 g) was dissolved in isopropanol (45 mL). Sixty percent aqueous sulfuric acid (0.67 ml) was added to the solution at 20° C. The reaction mixture was heated to reflux temperature for 2 hours. Then, the solution was cooled to room temperature and stirred at this temperature for additional 2 hours to obtain a white precipitate. The solid was collected by filtration, washed with IPA (2×10 ml) and dried at 50° C. in a vacuum oven for 15 hours to obtain 0.93 g (24%) of clopidogrel hydrogensulfate crystal Form IV.

Example 35

Preparation of Clopidogrel Hydrogensulfate Form IV

Clopidogrel base (2.85 g) was dissolved in isopropanol (43 mL). Forty percent aqueous sulfuric acid (1.67 mL) was added to the solution at 20° C. The reaction mixture was heated to reflex temperature for 2 hours. Then, the solution was cooled to room temperature and stirred at this temperature for additional 3.5 hours to obtain a white precipitate. The solid was collected by filtration, washed with IPA (2×10 ml) and dried at 50° C. in a vacuum oven for 14.5 hours to obtain 1.47 g (40%) of clopidogrel hydrogensulfate crystal Form IV.

Example 36

Preparation of Clopidogrel Hydrogensulfate Form IV

Clopidogrel base (2.95 g) was dissolved in isopropanol (45 ml). Forty percent aqueous sulfuric acid (1.15 mL) was added to the solution at 20° C. The reaction mixture was heated to reflux temperature for 2 hours. Then, the solution was cooled to room temperature and stirred at this temperature for an additional 3.5 hours to obtain a white precipitate. The solid was collected by filtration, washed with IPA (2×10 mL) and dried at 50° C. in a vacuum oven for 14.5 hours to obtain 0.49 g (13%) of clopidogrel hydrogensulfate crystal Form IV.

Example 37

Preparation of Clopidogrel Hydrogensulfate Form IV

Clopidogrel base (2.89 g) was dissolved in isopropanol (44 mL). Eighty percent aqueous sulfuric acid (0.42 mL) was added to the solution at 20° C. The reaction mixture was heated to reflux temperature for 2 hours. The solution was cooled to room temperature and stirred at this temperature for an additional 5 hours. Then half of the solvent was removed by evaporation under reduced pressure and the resulting solution was stored at room temperature for 45 minutes to obtain a white precipitate. The solid was collected by filtration, washed with IPA (3×10 ml) and dried at 50° C. in a vacuum oven for 15 hours to obtain 1.24 g (33%) of clopidogrel hydrogensulfate crystal Form IV.

Example 38

Preparation of Clopidogrel Hydrogensulfate Form IV

Clopidogrel base (2.96 g) was dissolved in isopropanol (IPA) (45 mL). Eighty percent aqueous sulfuric acid (0.65 mL) was added to the solution at 20° C. The reaction mixture was heated to reflux temperature for 2 hours. Then, the solution was cooled to room temperature and stirred at this temperature for an additional 1.5 hours to obtain a white precipitate. The solid was collected by filtration, washed with IPA (2×10 ml) and dried at 50° C. in a vacuum oven for 15 hours to obtain 3.24 g (84%) of clopidogrel hydrogensulfate crystal Form IV.

Example 39

Preparation of Clopidogrel Hydrogensulfate Form V

Clopidogrel hydrogensulfate (3 grams) was dissolved in 2-butanol (9 mL) at reflux temperature. The resulting solution was cooled to room temperature and methyl tert-butylether (MTBE) (40 mL) was added drop wise. The obtained mixture was stirred at room temperature for 72 hours. The solid was then filtered and dried at 50° C. in a vacuum oven for 24 hours to give 3.15 g of clopidogrel hydrogensulfate crystal Form V.

Example 40

Preparation of Clopidogrel Hydrogensulfate Form V

Clopidogrel hydrogensulfate (3 grams) was dissolved in 2-butanol (8 mL) at reflux temperature. The resulting solution was cooled to room temperature and the solvent was evaporated to dryness under reduced pressure. Then diethylether (DEE) (26 mL) was added drop wise and the obtained mixture was stirred at room temperature for 24 hours. The solid was then filtered and dried at 50° C. in a vacuum oven for 24 hours to give 3.08 g of clopidogrel hydrogensulfate crystal Form V.

Example 41

Preparation of Clopidogrel Hydrogensulfate Form V

Clopidogrel hydrogensulfate (3 grams) was dissolved in 2-butanol (14 mL) at reflux temperature. The resulting solution was cooled to room temperature. Then MTBE (35 mL) was added drop wise and the obtained mixture was stirred at room temperature for 16 hours. Additional MTBE (11 mL) was added and the suspension was stirred at room temperature for additional 2 hours. The solid was filtered, washed with MTBE (25 mL) and dried at 65° C. in a vacuum oven for 24 hours to give 2.95 g (98%) of clopidogrel hydrogensulfate crystal Form V.

Example 42

Preparation of Clopidogrel Hydrogensulfate Form V

Clopidogrel base (2.98 g) was dissolved in 2-butanol (23 mL). Ninety eight percent aqueous sulfuric acid (0.50 mL) was added to the solution at 20° C. The reaction mixture was heated to reflux temperature for 2 hours. The solution was cooled to room temperature and stirred at this temperature for an additional 3 hours. Then the solvent was evaporated to dryness under reduced pressure to obtain an oil. Then tert-butyl methyl ether (MTBE) (44 mL) was added to the oily residue and the resulting mixture was stirred at room temperature for 16 hours. The precipitate was collected by filtration, washed with MTBE (2×10 ml) and dried at 50° C. in a vacuum oven for 22.5 hours to obtain 3.38 g (87%) of clopidogrel hydrogensulfate crystal Form V.

Example 43

Preparation of Clopidogrel Hydrogensulfate Form V

Clopidogrel base (2.94 g) was dissolved in 2-butanol (23 mL). Ninety eight percent aqueous sulfuric acid (0.43 mL) was added to the solution at 20° C. The reaction mixture was heated to reflex temperature for 2 hours. The solution was cooled to room temperature and stirred at this temperature for additional 1.5 hours. Then the solvent was evaporated to dryness under reduced pressure to obtain oil. Then diethyl ether (DEE) (40 ml) was added to the oily residue and the resulting mixture was stirred at room temperature for 16 hours. The precipitate was collected by filtration, washed with DEE (2×10 mL) and dried at 50° C. in a vacuum oven for 19 hours to obtain 2.11 g (55%) of clopidogrel hydrogensulfate crystal Form V.

Example 44

Preparation of Clopidogrel Hydrogensulfate Form VI

Clopidogrel base (2.86 g, 1 eq.) was dissolved in 1-Propanol (22.6 mL). Eighty percent aqueous sulfuric acid (0.59 mL, 0.66 eq.) was added to the solution at 20° C. The reaction mixture was heated to reflux temperature for 2 hours. Then, the solution was cooled to room temperature and stirred at this temperature for additional 16 hours. The solvent was evaporated to dryness under reduced pressure to obtain an oily residue. To the residue, MTBE (50 mL) was added and the resulting mixture was stirred at room temperature for 24 hours during which a massive precipitate was formed. The white solid was collected by filtration, washed with MTBE (2×10 mL) and dried at 50° C. in a vacuum oven for 30 hours to obtain 2.58 g (69%) of clopidogrel hydrogensulfate crystal Form VI.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 can be used as a guidance. All references mentioned herein are incorporated in their entirety.

What is claimed is:

1. Clopidopel hydrogensulfate characterized by a powder X-ray diffraction pattern with peaks at about 8.3, 9.1, 23.2 and 23.6±0.2 degrees theta and a FTIR spectrum with peaks at about 959, 1061, 1430, 1751, 1757 and 3119 cm$^{-1}$.

2. The clopidogrel hydrogensulfate of claim 1 further characterized by a FTIR spectrum as of FIG. 14.

3. The clopidogrel hydrogensulfate of claim 1 further characterized by a powder X-ray diffraction pattern as of FIG. 12.

4. A process for preparing clopidogrel hydrogensulfate of claim 1 comprising the steps of:
   a) preparing a solution of clopidogrel hydrogensulfate in 1-propanol,
   b) removing the 1-propanol from the solution to obtain a residue;
   c) admixing an antisolvent with the residue to precipitate clopidogrel hydrogensulfate; and
   d) separating the clopidogrel hydrogensulfate.

5. The process of claim 4, wherein the process results in a clopidogrel hydrogensulfate with a purity of at least about 99% as measured by area percentage with HPLC.

6. The process of claim 4, wherein the antisolvent is an ether.

7. The process of claim 6, wherein the ether is selected from the group dimethyl-ether, diethyl-ether, dipropyl-ether, diisopropyl-ether, di-l-butyl-ether, di-2-butyl-ether and di-t-butyl-ether.

8. The process of claim 7, wherein the ether is diethyl ether.

9. The process of claim 4, wherein step c) includes contacting with hydrosulfuric acid in 1-propanol.

10. A process for preparing clopidogrel hydrogensulfate Form II comprising the steps of:
    a) preparing a solution of clopidogrel hydrogensulfate in a solvent selected from the group consisting of dichloromethane, 1,4-dioxane, toluene, chloroform, ethyl acetate, methylethyl ketone and t-butylmethyl ether;
    b) precipitating clopidogrel hydrogensulfate from the solution; and
    c) separating the clopidogrel hydrogensulfate.

11. The process of claim 10, wherein the solvent is dichloromethane.

12. The process of claim 10, wherein the solvent is 1,4-dioxane.

13. The process of claim 10, wherein the solvent is toluene.

14. The process of claim 10, wherein the solvent is chloroform.

15. The process of claim 10, wherein the solvent is ethyl acetate.

16. The process of claim 10, wherein the solvent is methylethyl ketone.

17. The process of claim 10, wherein the solvent is t-butylmethyl ether.

18. A process for preparing clopidogrel hydrogensulfate Form II comprising the steps of:
  a) preparing a solution of clopidogrel hydrogensulfate in acetonitrile;
  b) admixing the solution with an antisolvent to precipitate clopidogrel hydrogensulfate; and
  c) separating the precipitate.

19. The process of claim 18, wherein the admixing involves addition of the solution to the antisolvent.

20. The process of claim 18, wherein the clopidogrel hydrogensulfate used to prepare the solution is amorphous clopidogrel hydrogensulfate.

21. The process of claim 18, wherein the antisolvent is an ether.

22. The process of claim 21, wherein the ether is selected from the group dimethyl-ether, diethyl-ether, dipropyl-ether diisopropyl-ether, di-l-butyl-ether, di-2-butyl-ether and di-t-butyl-ether.

23. The process of claim 22, wherein the ether is diethyl ether.

24. The process of claim 23, wherein preparing a solution includes converting clopidogrel base to clopidogrel hydrogensulfate by contact with hydrosulfuric acid in solvent of the resulting solution.

25. Crystalline Clopidogrel hydrogensulfate 1-propanolate.

26. The clopidogrel hydrogensulfate of claim 25, wherein the 1-propanol content is about 6% by weight.

27. Crystalline clopidogrel hydrogensulfate 1-butanol solvate.

28. The clopidogrel hydrogensulfate of claim 27, wherein the 1-butanol content is about 7% to about 8% by weight.

29. Crystalline clopidogrel hydrogensulfate isopropanol solvate.

30. The clopidogrel hydrogensulfate of claim 29, wherein the isopropanol content is about 3% to about 9% by weight.

31. Crystalline clopidogrel hydrogensulfate 2-butanol solvate.

32. The clopidogrel hydrogensulfate of claim 31, wherein the 2-butanol content is about 9% to about 10% by weight.

33. A process for preparing crystalline clopidogrel hydrogensulfate Form III comprising the steps of:
  a) preparing a solution of clopidogrel hydrogensulfate in 1-butanol;
  b) removing the 1-butanol from the solution to obtain a residue;
  c) adding in any order an antisolvent to the residue to precipitate clopidogrel hydrogensulfate; and
  d) separating the clopidogrel hydrogensulfate.

34. The process of claim 33, wherein removing is carried out with evaporation.

35. The process of claim 33, wherein the antisolvent is an ether.

* * * * *

UNITED STATES PATENT AND TRADEMARK OFFICE
CERTIFICATE OF CORRECTION

PATENT NO.      : 7,074,928 B2
APPLICATION NO. : 10/339008
DATED           : July 11, 2006
INVENTOR(S)     : Lifshitz-Liron et al.

It is certified that error appears in the above-identified patent and that said Letters Patent is hereby corrected as shown below:

Cover page, column 2, reference cited, foreign patent document, change "WO 98/09286" to -- WO 98/39286 --

Column 1, line 7-11, change "U.S. Pat. No. 6,767,915" to -- U.S. Pat. No. 6,767,913 --

Column 2, line 7, change "$C_{16}H_{16}Cl\ NO_2S.H_2SO_4$" to -- $C_{16}H_{16}Cl\ NO_2S \cdot H_2SO_4$ --

Column 15, line 49-50, change "DSC Mettler 821e Stare." to -- DSC Mettler 821e Star$^e$ --

Column 16, line 61, change "crystal Form I." to -- crystal Form II. --

Signed and Sealed this

Thirteenth Day of November, 2007

JON W. DUDAS
*Director of the United States Patent and Trademark Office*